(12) United States Patent
Milliman

(10) Patent No.: US 8,181,840 B2
(45) Date of Patent: May 22, 2012

(54) TISSUE TENSIONER ASSEMBLY AND APPROXIMATION MECHANISM FOR SURGICAL STAPLING DEVICE

(75) Inventor: Keith L. Milliman, Bethel, CT (US)

(73) Assignee: Tyco Healthcare Group LP, Mansfield, MA (US)

( * ) Notice: Subject to any disclaimer, the term of this patent is extended or adjusted under 35 U.S.C. 154(b) by 1734 days.

(21) Appl. No.: 11/081,373

(22) Filed: Mar. 16, 2005

(65) Prior Publication Data

US 2005/0205640 A1  Sep. 22, 2005

Related U.S. Application Data

(60) Provisional application No. 60/554,556, filed on Mar. 19, 2004, provisional application No. 60/554,562, filed on Mar. 19, 2004.

(51) Int. Cl.
*A61B 17/115* (2006.01)
*A61B 17/068* (2006.01)

(52) U.S. Cl. .................... 227/179.1; 227/175.1; 227/19

(58) Field of Classification Search ............... 227/19, 227/175.1–182.1; 606/219
See application file for complete search history.

(56) References Cited

U.S. PATENT DOCUMENTS

| | | | |
|---|---|---|---|
| 3,388,847 A | 6/1968 | Kasulin et al. |
| 3,552,626 A | 1/1971 | Astafiev |
| 3,638,652 A | 2/1972 | Kelley |
| 4,198,982 A | 4/1980 | Fortner et al. |
| 4,207,898 A | 6/1980 | Becht |
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |

(Continued)

FOREIGN PATENT DOCUMENTS

CA         908529         8/1972

(Continued)

OTHER PUBLICATIONS

European Search Report for EP 05 00 5966, date of Mailing Aug. 19, 2005 (3 pgs).

(Continued)

*Primary Examiner* — Lindsay Low

(57) ABSTRACT

A surgical stapling device having an approximation mechanism for treating hollow tissue organs is provided. The stapling device includes a handle, a body portion extending distally from the handle, a distal head portion at a distal end of the body portion, and an approximation mechanism. The head portion includes an anvil assembly having an anvil head and an anvil shaft. The approximation mechanism includes a rotatable approximation knob, a first member, and a second member. The rotatable approximation knob is operably connected to the first member to effect movement the first member over a first distance. The second member is rotatably coupled to a proximal end of the anvil shaft of the anvil assembly to operably connect the anvil shaft to the first member such that movement of the first member over the first distance effects movement of the anvil shaft in relation to the first member over a second distance.

13 Claims, 31 Drawing Sheets

U.S. PATENT DOCUMENTS

| | | | |
|---|---|---|---|
| 4,505,272 A | 3/1985 | Utyamyshev et al. | |
| 4,505,414 A | 3/1985 | Filipi | |
| 4,550,870 A | 11/1985 | Krumme et al. | |
| 4,573,468 A | 3/1986 | Conta et al. | |
| 4,576,167 A | 3/1986 | Noiles | |
| 4,592,354 A | 6/1986 | Rothfuss | |
| 4,603,693 A | 8/1986 | Conta et al. | |
| 4,606,343 A | 8/1986 | Conta et al. | |
| 4,646,745 A | 3/1987 | Noiles | |
| 4,665,917 A * | 5/1987 | Clanton et al. | 606/153 |
| 4,667,673 A | 5/1987 | Li | |
| 4,671,445 A | 6/1987 | Barker et al. | |
| 4,700,703 A | 10/1987 | Resnick et al. | |
| 4,703,887 A | 11/1987 | Clanton et al. | |
| 4,708,141 A | 11/1987 | Inoue et al. | |
| 4,754,909 A | 7/1988 | Barker et al. | |
| 4,817,847 A | 4/1989 | Redtenbacher et al. | |
| 4,873,977 A | 10/1989 | Avant et al. | |
| 4,893,622 A | 1/1990 | Green et al. | |
| 4,903,697 A | 2/1990 | Resnick et al. | |
| 4,907,591 A | 3/1990 | Vasconcellos et al. | |
| 4,917,114 A | 4/1990 | Green et al. | |
| 4,957,499 A | 9/1990 | Lipatov et al. | |
| 5,005,749 A | 4/1991 | Aranyi | |
| 5,042,707 A | 8/1991 | Taheri | |
| 5,047,039 A | 9/1991 | Avant et al. | |
| 5,104,025 A | 4/1992 | Main et al. | |
| 5,119,983 A | 6/1992 | Green et al. | |
| 5,122,156 A | 6/1992 | Granger et al. | |
| 5,139,513 A | 8/1992 | Segato | |
| 5,158,222 A | 10/1992 | Green et al. | |
| 5,188,638 A | 2/1993 | Tzakis | |
| 5,193,731 A | 3/1993 | Aranyi | |
| 5,197,648 A | 3/1993 | Gingold | |
| 5,197,649 A | 3/1993 | Bessler et al. | |
| 5,205,459 A | 4/1993 | Brinkerhoff et al. | |
| 5,221,036 A | 6/1993 | Takase | |
| 5,222,963 A | 6/1993 | Brinkerhoff et al. | |
| 5,253,793 A | 10/1993 | Green et al. | |
| 5,261,920 A | 11/1993 | Main et al. | |
| 5,271,543 A | 12/1993 | Grant et al. | |
| 5,271,544 A | 12/1993 | Fox et al. | |
| 5,275,322 A | 1/1994 | Brinkerhoff et al. | |
| 5,282,810 A | 2/1994 | Allen et al. | |
| 5,285,944 A | 2/1994 | Green et al. | |
| 5,285,945 A | 2/1994 | Brinkerhoff et al. | |
| 5,292,053 A | 3/1994 | Bilotti et al. | |
| 5,309,927 A | 5/1994 | Welch | |
| 5,312,024 A | 5/1994 | Grant et al. | |
| 5,314,435 A | 5/1994 | Green et al. | |
| 5,314,436 A | 5/1994 | Wilk | |
| 5,330,486 A | 7/1994 | Wilk | |
| 5,333,773 A | 8/1994 | Main et al. | |
| 5,344,059 A | 9/1994 | Green et al. | |
| 5,346,115 A | 9/1994 | Perouse et al. | |
| 5,348,259 A | 9/1994 | Blanco et al. | |
| 5,350,104 A | 9/1994 | Main et al. | |
| 5,355,897 A | 10/1994 | Pietrafitta et al. | |
| 5,360,154 A | 11/1994 | Green | |
| 5,368,215 A | 11/1994 | Green et al. | |
| 5,392,979 A | 2/1995 | Green et al. | |
| 5,395,030 A | 3/1995 | Kuramoto et al. | |
| 5,403,333 A | 4/1995 | Kaster et al. | |
| 5,404,870 A | 4/1995 | Brinkerhoff et al. | |
| 5,411,508 A | 5/1995 | Bessler et al. | |
| 5,433,721 A | 7/1995 | Hooven et al. | |
| 5,437,684 A | 8/1995 | Calabrese et al. | |
| 5,439,156 A | 8/1995 | Grant et al. | |
| 5,443,198 A | 8/1995 | Viola et al. | |
| 5,445,644 A | 8/1995 | Pietrafitta et al. | |
| 5,447,514 A | 9/1995 | Gerry et al. | |
| 5,454,825 A | 10/1995 | Van Leeuwen et al. | |
| 5,470,006 A | 11/1995 | Rodak | |
| 5,474,223 A | 12/1995 | Viola et al. | |
| 5,497,934 A | 3/1996 | Brady et al. | |
| 5,522,534 A | 6/1996 | Viola et al. | |
| 5,533,661 A | 7/1996 | Main et al. | |
| 5,588,579 A | 12/1996 | Schnut et al. | |
| 5,609,285 A | 3/1997 | Grant et al. | |
| 5,632,433 A | 5/1997 | Grant et al. | |
| 5,639,008 A | 6/1997 | Gallagher et al. | |
| 5,658,300 A | 8/1997 | Bito et al. | |
| 5,669,918 A | 9/1997 | Balazs et al. | |
| 5,685,474 A | 11/1997 | Seeber | |
| 5,709,335 A | 1/1998 | Heck | |
| 5,715,987 A | 2/1998 | Kelley et al. | |
| 5,718,360 A | 2/1998 | Green et al. | |
| 5,720,755 A | 2/1998 | Dakov | |
| 5,732,872 A | 3/1998 | Bolduc et al. | |
| 5,758,814 A | 6/1998 | Gallagher et al. | |
| 5,799,857 A | 9/1998 | Robertson et al. | |
| 5,836,503 A | 11/1998 | Ehrenfels et al. | |
| 5,839,639 A | 11/1998 | Sauer et al. | |
| 5,855,312 A | 1/1999 | Toledano | |
| 5,860,581 A | 1/1999 | Robertson et al. | |
| 5,868,760 A | 2/1999 | McGuckin, Jr. | |
| 5,881,943 A | 3/1999 | Heck et al. | |
| 5,915,616 A | 6/1999 | Viola et al. | |
| 5,947,363 A | 9/1999 | Bolduc et al. | |
| 5,951,576 A | 9/1999 | Wakabayashi | |
| 5,957,363 A | 9/1999 | Heck | |
| 5,993,468 A | 11/1999 | Rygaard | |
| 6,050,472 A | 4/2000 | Shibata | |
| 6,053,390 A | 4/2000 | Green et al. | |
| 6,068,636 A | 5/2000 | Chen | |
| 6,083,241 A | 7/2000 | Longo et al. | |
| 6,102,271 A | 8/2000 | Longo et al. | |
| 6,117,148 A | 9/2000 | Ravo et al. | |
| 6,119,913 A | 9/2000 | Adams et al. | |
| 6,126,058 A | 10/2000 | Adams et al. | |
| 6,149,667 A | 11/2000 | Hovland et al. | |
| 6,176,413 B1 | 1/2001 | Heck et al. | |
| 6,179,195 B1 | 1/2001 | Adams et al. | |
| 6,193,129 B1 | 2/2001 | Bittner et al. | |
| 6,203,553 B1 | 3/2001 | Robertson et al. | |
| 6,209,773 B1 | 4/2001 | Bolduc et al. | |
| 6,241,140 B1 | 6/2001 | Adams et al. | |
| 6,253,984 B1 | 7/2001 | Heck et al. | |
| 6,258,107 B1 | 7/2001 | Balazs et al. | |
| 6,264,086 B1 | 7/2001 | McGuckin, Jr. | |
| 6,269,997 B1 | 8/2001 | Balazs et al. | |
| 6,279,809 B1 | 8/2001 | Nicolo | |
| 6,302,311 B1 | 10/2001 | Adams et al. | |
| 6,338,737 B1 | 1/2002 | Toledano | |
| 6,343,731 B1 | 2/2002 | Adams et al. | |
| 6,387,105 B1 | 5/2002 | Gifford, III et al. | |
| 6,398,795 B1 | 6/2002 | McAlister et al. | |
| 6,402,008 B1 | 6/2002 | Lucas | |
| 6,450,390 B2 | 9/2002 | Heck et al. | |
| 6,478,210 B2 | 11/2002 | Adams et al. | |
| 6,488,197 B1 | 12/2002 | Whitman | |
| 6,491,201 B1 | 12/2002 | Whitman | |
| 6,494,877 B2 | 12/2002 | Odell et al. | |
| 6,503,259 B2 | 1/2003 | Huxel et al. | |
| 6,517,566 B1 | 2/2003 | Hovland et al. | |
| 6,520,398 B2 | 2/2003 | Nicolo | |
| 6,533,157 B1 | 3/2003 | Whitman | |
| 6,578,751 B2 | 6/2003 | Hartwick | |
| 6,585,144 B2 | 7/2003 | Adams et al. | |
| 6,588,643 B2 | 7/2003 | Bolduc et al. | |
| 6,592,596 B1 | 7/2003 | Geitz | |
| 6,601,749 B2 | 8/2003 | Sullivan et al. | |
| 6,605,078 B2 | 8/2003 | Adams | |
| 6,623,227 B2 | 9/2003 | Scott et al. | |
| 6,626,921 B2 | 9/2003 | Blatter et al. | |
| 6,629,630 B2 | 10/2003 | Adams | |
| 6,631,837 B1 | 10/2003 | Heck | |
| 6,632,227 B2 | 10/2003 | Adams | |
| 6,632,237 B2 | 10/2003 | Ben-David et al. | |
| 6,659,327 B2 | 12/2003 | Heck et al. | |
| 6,676,671 B2 | 1/2004 | Robertson et al. | |
| 6,681,979 B2 | 1/2004 | Whitman | |
| 6,685,079 B2 | 2/2004 | Sharma et al. | |
| 6,695,198 B2 | 2/2004 | Adams et al. | |
| 6,695,199 B2 | 2/2004 | Whitman | |
| 6,716,222 B2 | 4/2004 | McAlister et al. | |
| 6,716,233 B1 | 4/2004 | Whitman | |

| | | |
|---|---|---|
| 6,742,692 B2 | 6/2004 | Hartwick |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,827,246 B2 | 12/2004 | Sullivan et al. |
| 6,840,423 B2 | 1/2005 | Adams et al. |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,959,851 B2 * | 11/2005 | Heinrich .................... 227/175.1 |
| 7,234,624 B2 * | 6/2007 | Gresham et al. ........... 227/179.1 |
| 2001/0000903 A1 | 5/2001 | Heck et al. |
| 2001/0010320 A1 | 8/2001 | Bolduc et al. |
| 2001/0054636 A1 | 12/2001 | Nicolo |
| 2002/0020732 A1 | 2/2002 | Adams et al. |
| 2002/0047036 A1 | 4/2002 | Sullivan et al. |
| 2002/0063143 A1 | 5/2002 | Adams et al. |
| 2002/0185516 A1 | 12/2002 | Heck et al. |
| 2002/0185517 A1 | 12/2002 | Vresh et al. |
| 2003/0019905 A1 | 1/2003 | Adams et al. |
| 2003/0047582 A1 | 3/2003 | Sonnenschein et al. |
| 2003/0057251 A1 | 3/2003 | Hartwick |
| 2003/0065342 A1 | 4/2003 | Nobis et al. |
| 2003/0073981 A1 | 4/2003 | Whitman et al. |
| 2003/0089757 A1 | 5/2003 | Whitman |
| 2003/0111507 A1 | 6/2003 | Nunez |
| 2003/0127491 A1 | 7/2003 | Adams et al. |
| 2003/0132267 A1 | 7/2003 | Adams et al. |
| 2003/0144675 A1 | 7/2003 | Nicolo |
| 2003/0178465 A1 | 9/2003 | Bilotti et al. |
| 2003/0183671 A1 | 10/2003 | Mooradian et al. |
| 2003/0192936 A1 | 10/2003 | Hartwick |
| 2003/0192937 A1 | 10/2003 | Sullivan et al. |
| 2003/0201301 A1 | 10/2003 | Bolduc et al. |
| 2003/0218047 A1 | 11/2003 | Sharma et al. |
| 2003/0222117 A1 | 12/2003 | Orban, III |
| 2004/0092960 A1 | 5/2004 | Abrams et al. |
| 2004/0092974 A1 | 5/2004 | Gannoe et al. |
| 2004/0118896 A1 | 6/2004 | Sharma et al. |
| 2004/0134964 A1 | 7/2004 | Adams et al. |
| 2004/0153124 A1 | 8/2004 | Whitman |
| 2004/0232198 A1 | 11/2004 | Adams et al. |
| 2005/0051597 A1 | 3/2005 | Toledano |
| 2005/0067454 A1 | 3/2005 | Vresh et al. |
| 2005/0087580 A1 | 4/2005 | Orban, III |
| 2005/0107813 A1 | 5/2005 | Gilete Garcia |
| 2005/0116009 A1 | 6/2005 | Milliman |
| 2005/0125009 A1 | 6/2005 | Perry et al. |
| 2005/0143758 A1 | 6/2005 | Abbott et al. |
| 2005/0145674 A1 | 7/2005 | Sonnenschein et al. |
| 2005/0145675 A1 | 7/2005 | Hartwick et al. |
| 2006/0085033 A1 * | 4/2006 | Criscuolo et al. ............. 606/219 |
| 2006/0151567 A1 * | 7/2006 | Roy .......................... 227/175.1 |
| 2007/0038248 A1 * | 2/2007 | Heinrch ........................ 606/219 |
| 2007/0075117 A1 * | 4/2007 | Milliman et al. .......... 227/179.1 |

FOREIGN PATENT DOCUMENTS

| | | |
|---|---|---|
| DE | 1057729 | 5/1959 |
| DE | 3301713 | 11/1989 |
| EP | 0152382 | 8/1985 |
| EP | 0173451 | 3/1986 |
| EP | 0190022 | 8/1986 |
| EP | 282157 | 9/1988 |
| EP | 0503689 | 9/1992 |
| FR | 1461464 | 12/1966 |
| FR | 1588250 | 4/1970 |
| FR | 1136020 | 12/1979 |
| FR | 2443239 | 12/1979 |
| GB | 1185292 | 3/1970 |
| GB | 2016991 | 9/1979 |
| GB | 2070499 | 9/1981 |
| NL | 7711347 | 10/1977 |
| WO | 8706448 | 11/1987 |
| WO | 8900406 | 1/1989 |
| WO | 9006085 | 6/1990 |
| WO | WO 02/080781 | 10/2002 |
| WO | WO02/080781 A | 10/2002 |
| WO | WO 2005/009216 | 2/2005 |

OTHER PUBLICATIONS

European Search Report for EP 05 00 5966, date of Completion of the search Oct. 17, 2005 (6 pgs).

* cited by examiner

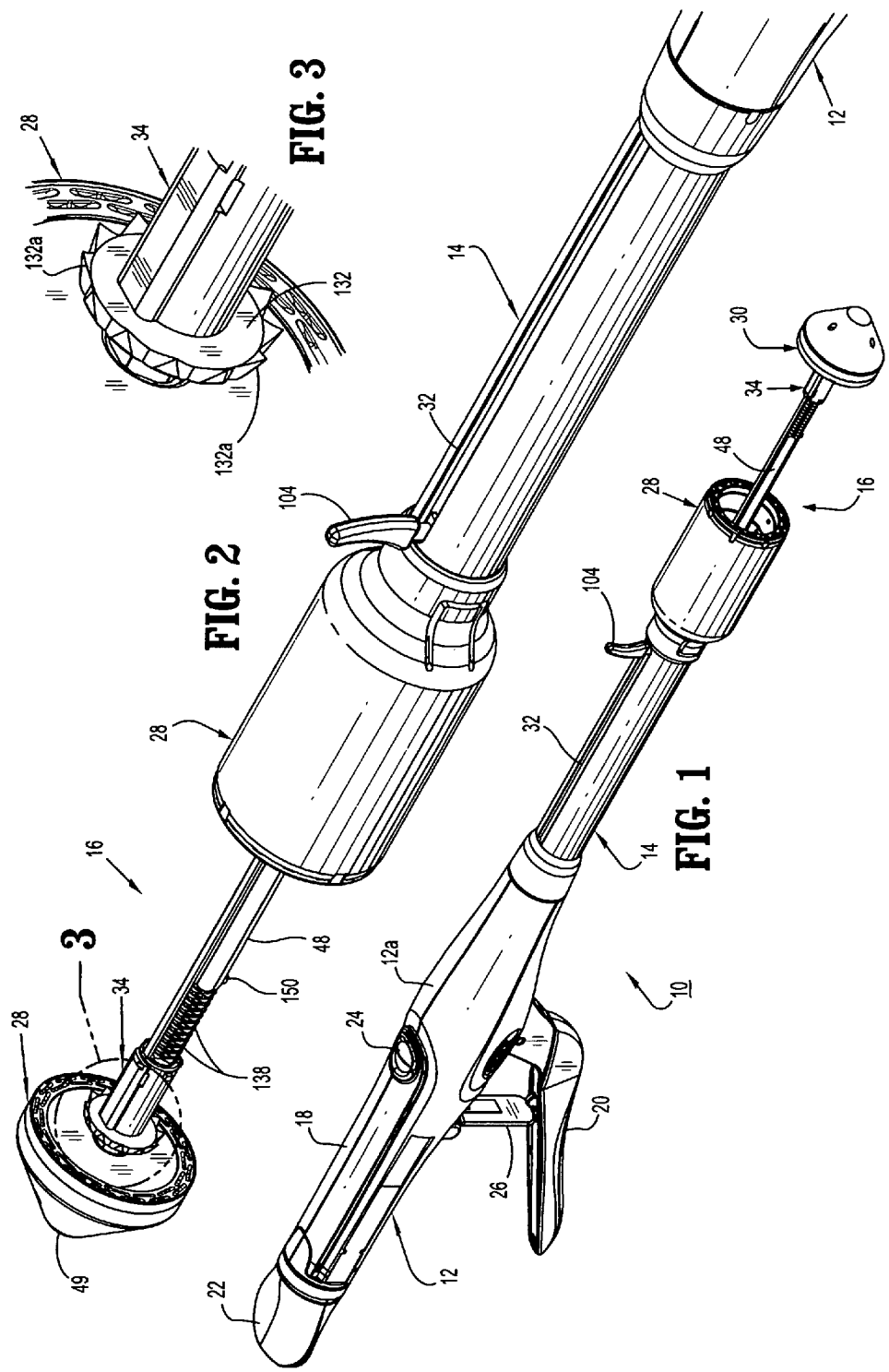

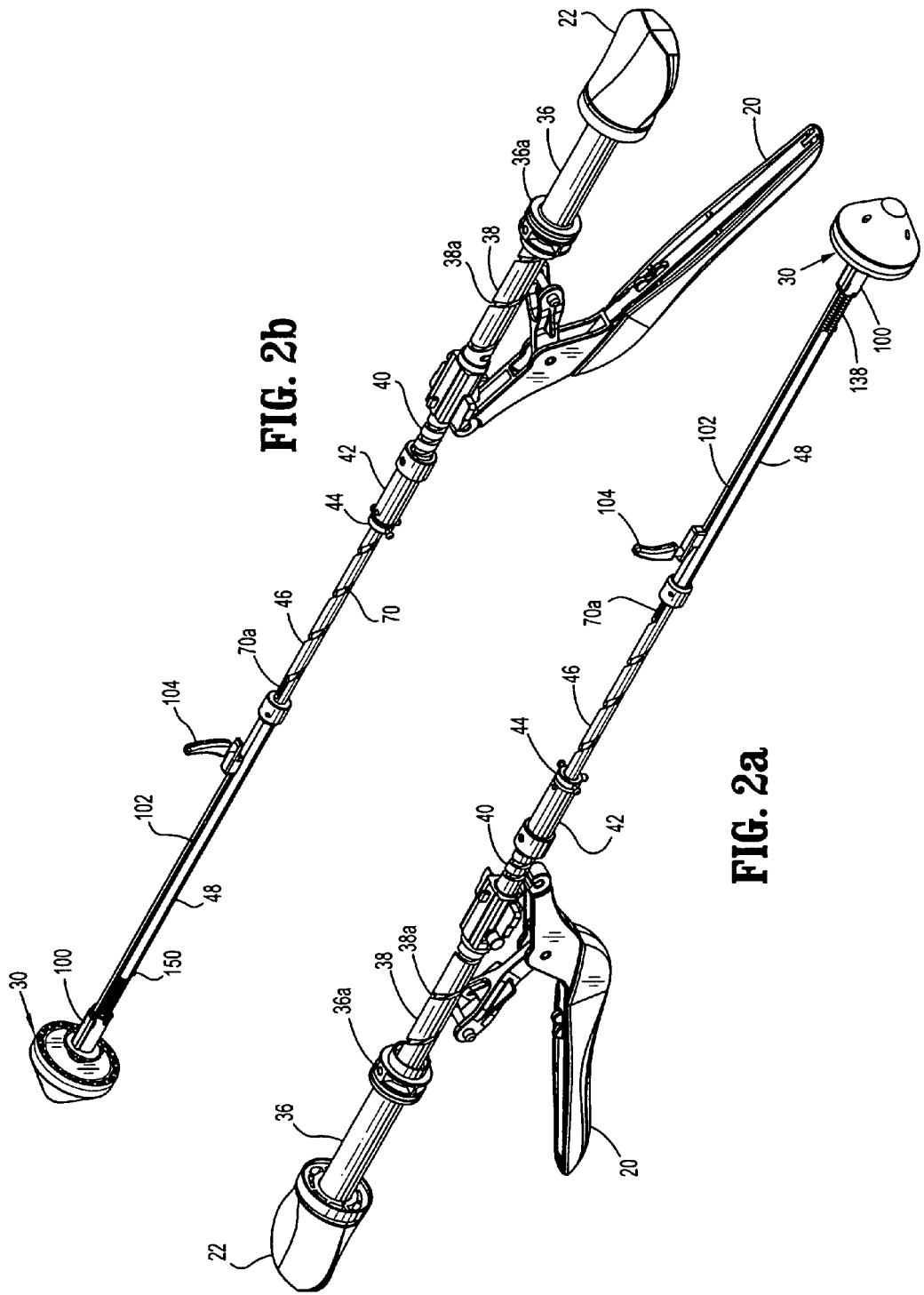

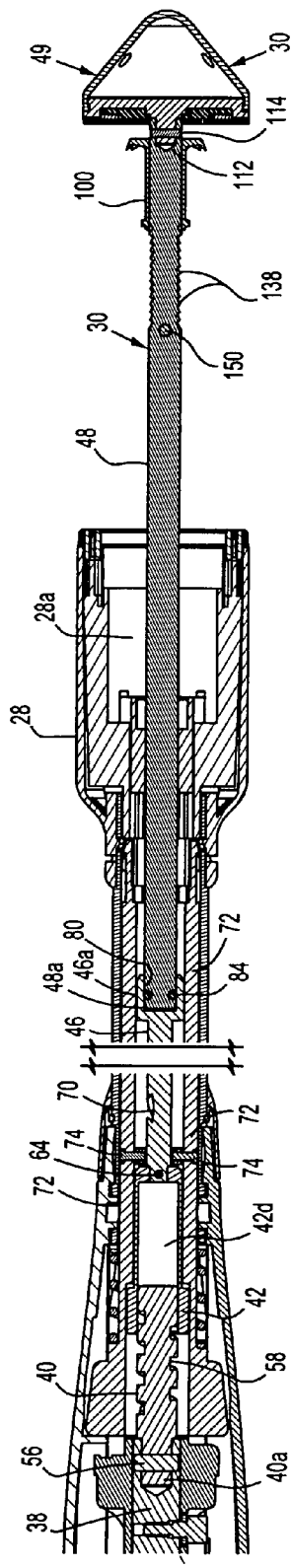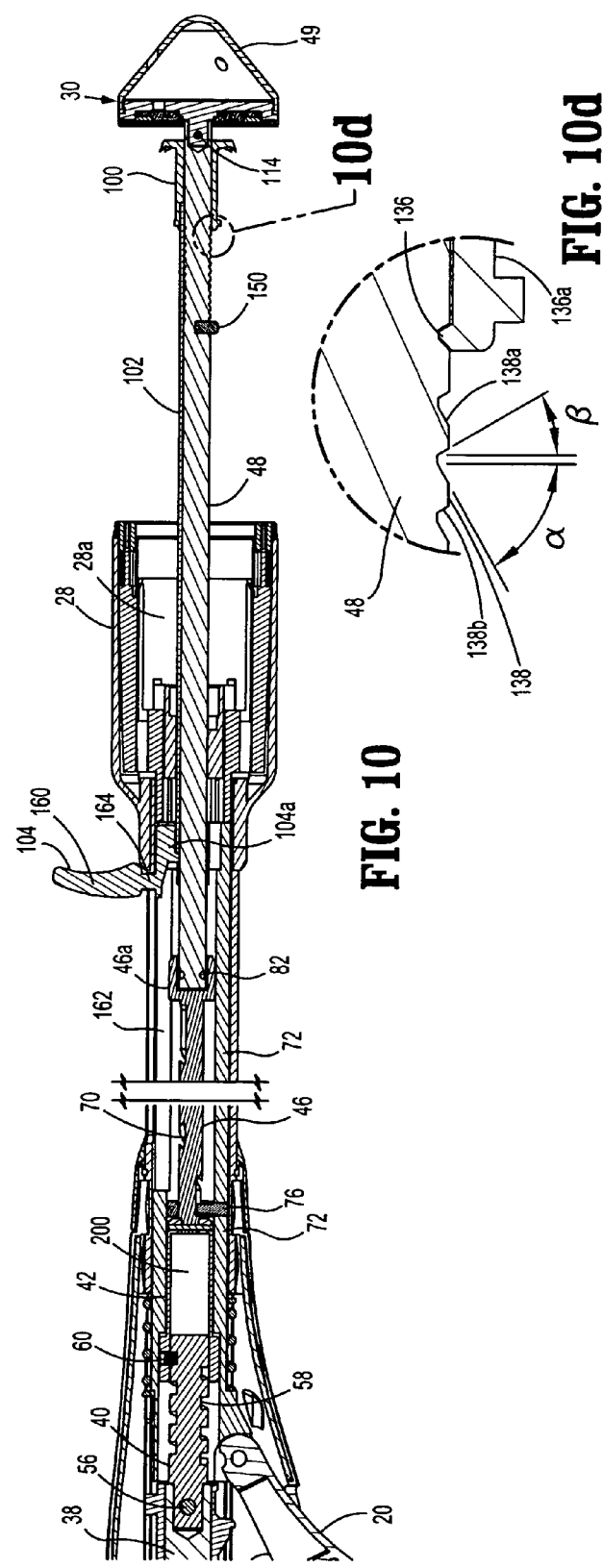

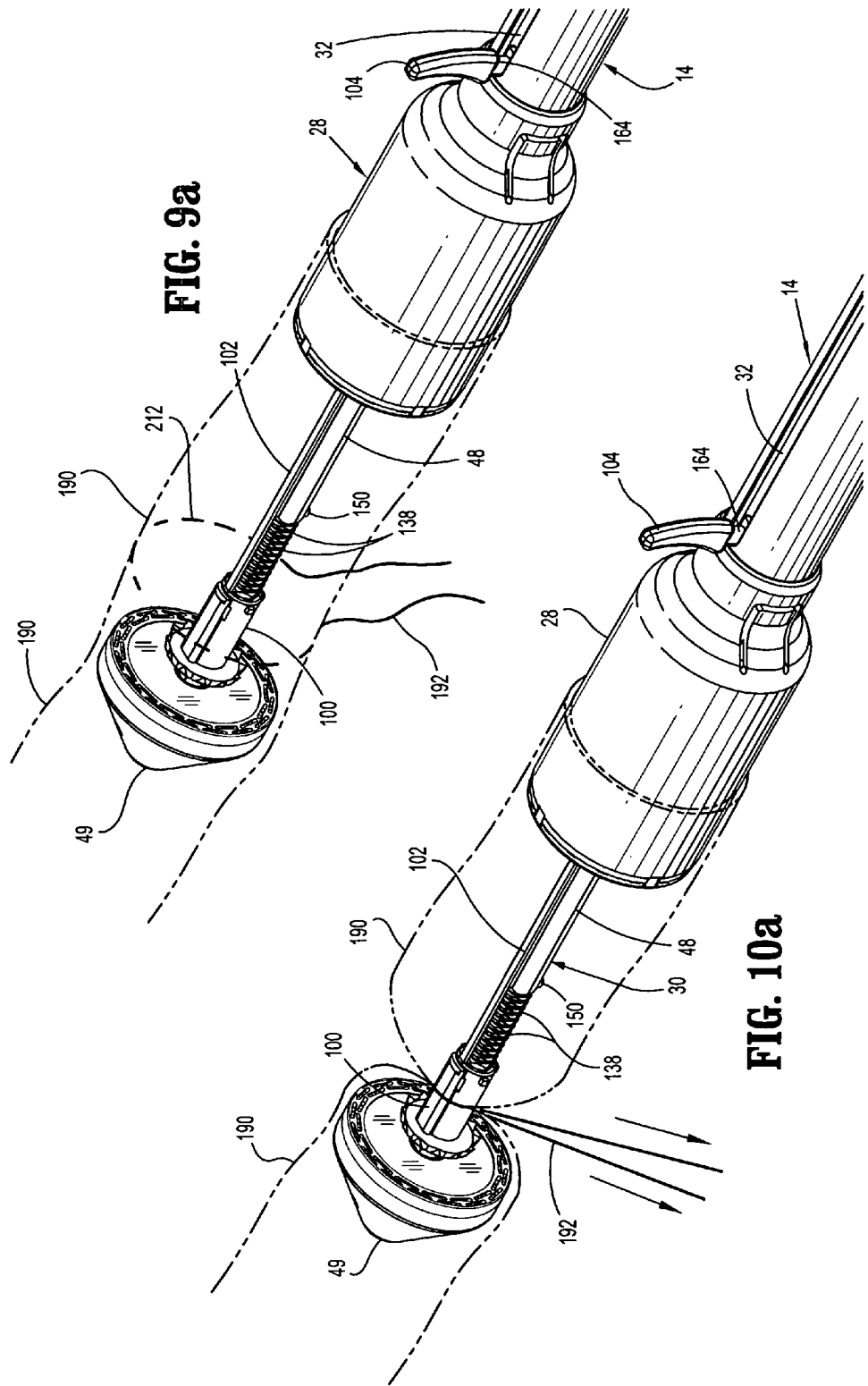

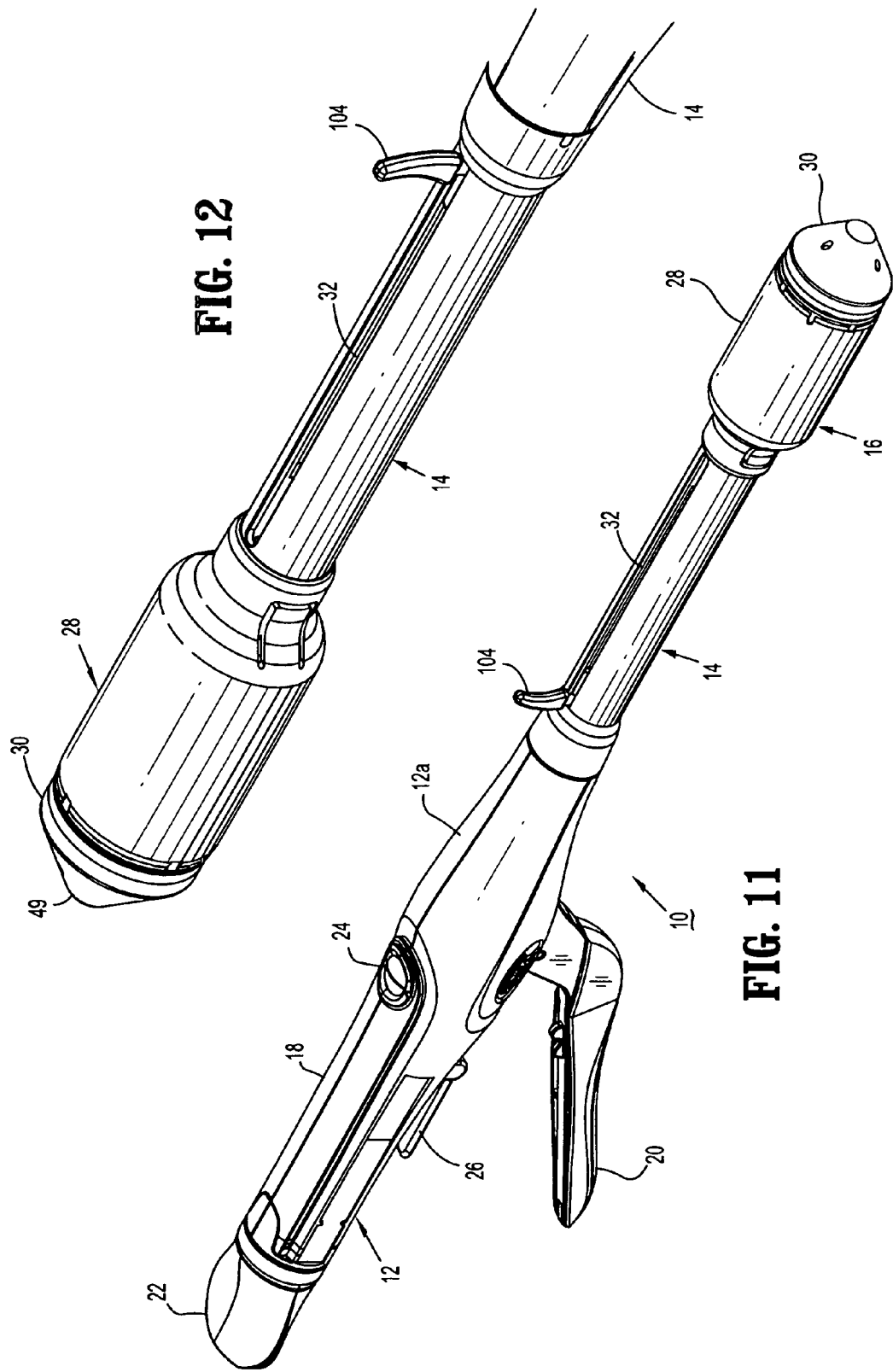

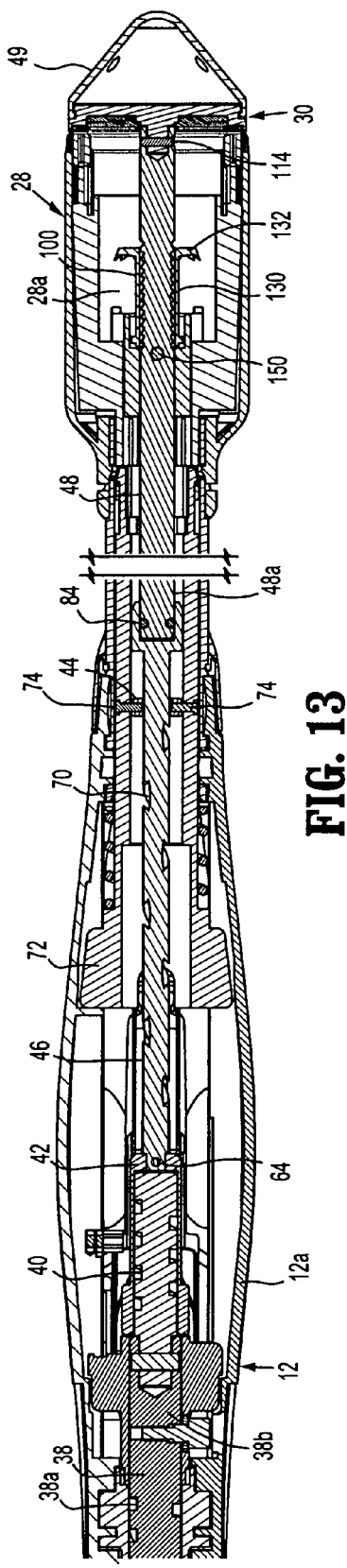
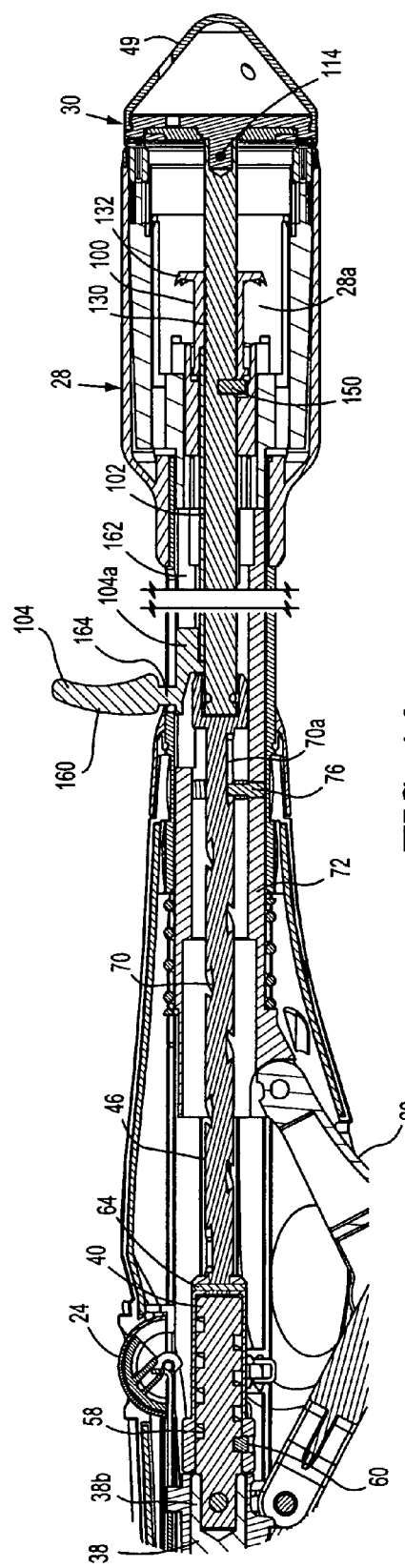
FIG. 13
FIG. 14

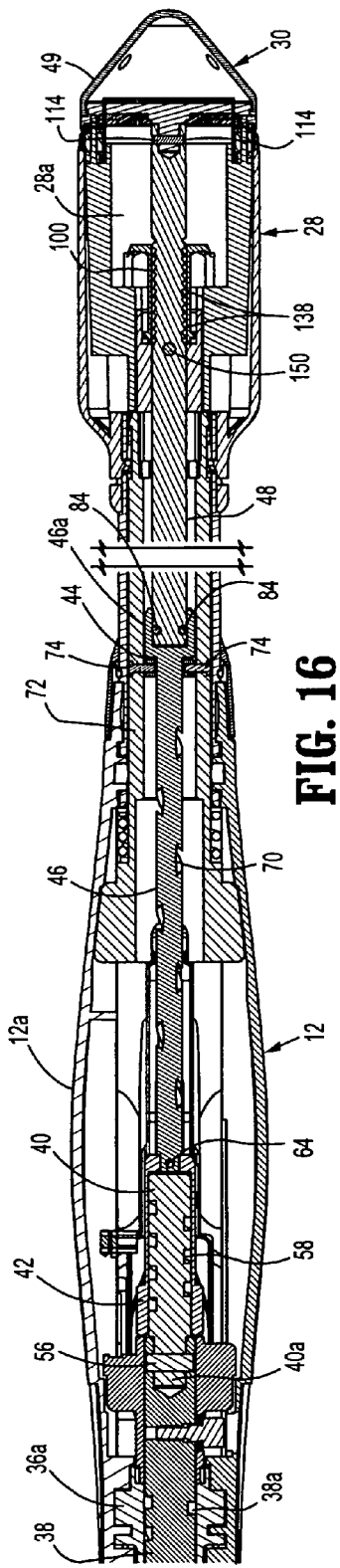
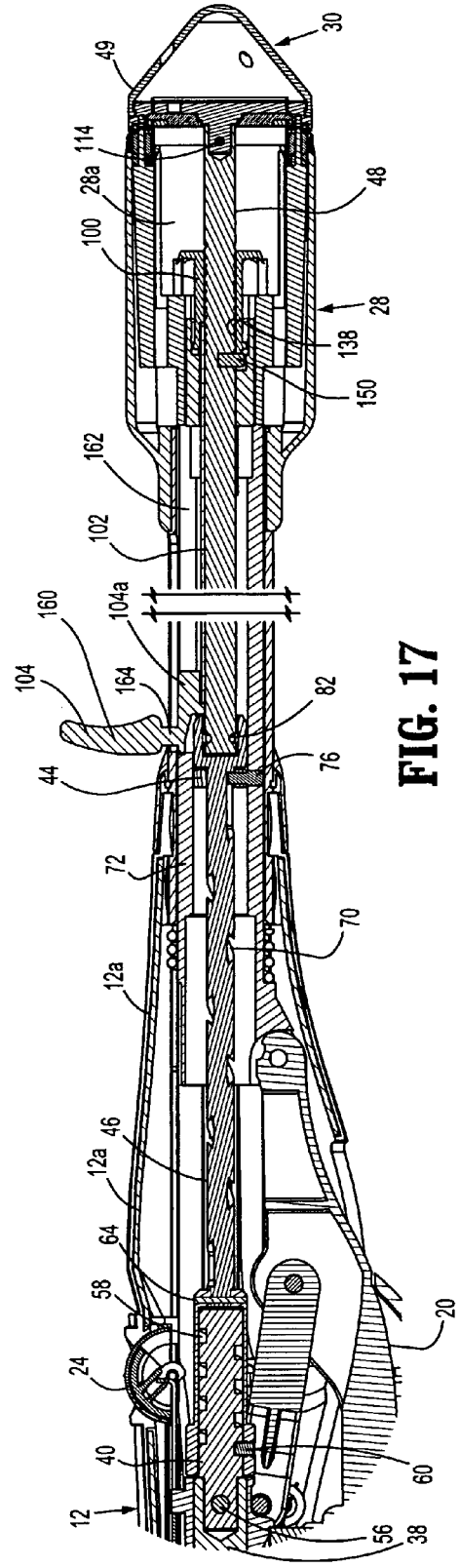
FIG. 16
FIG. 17

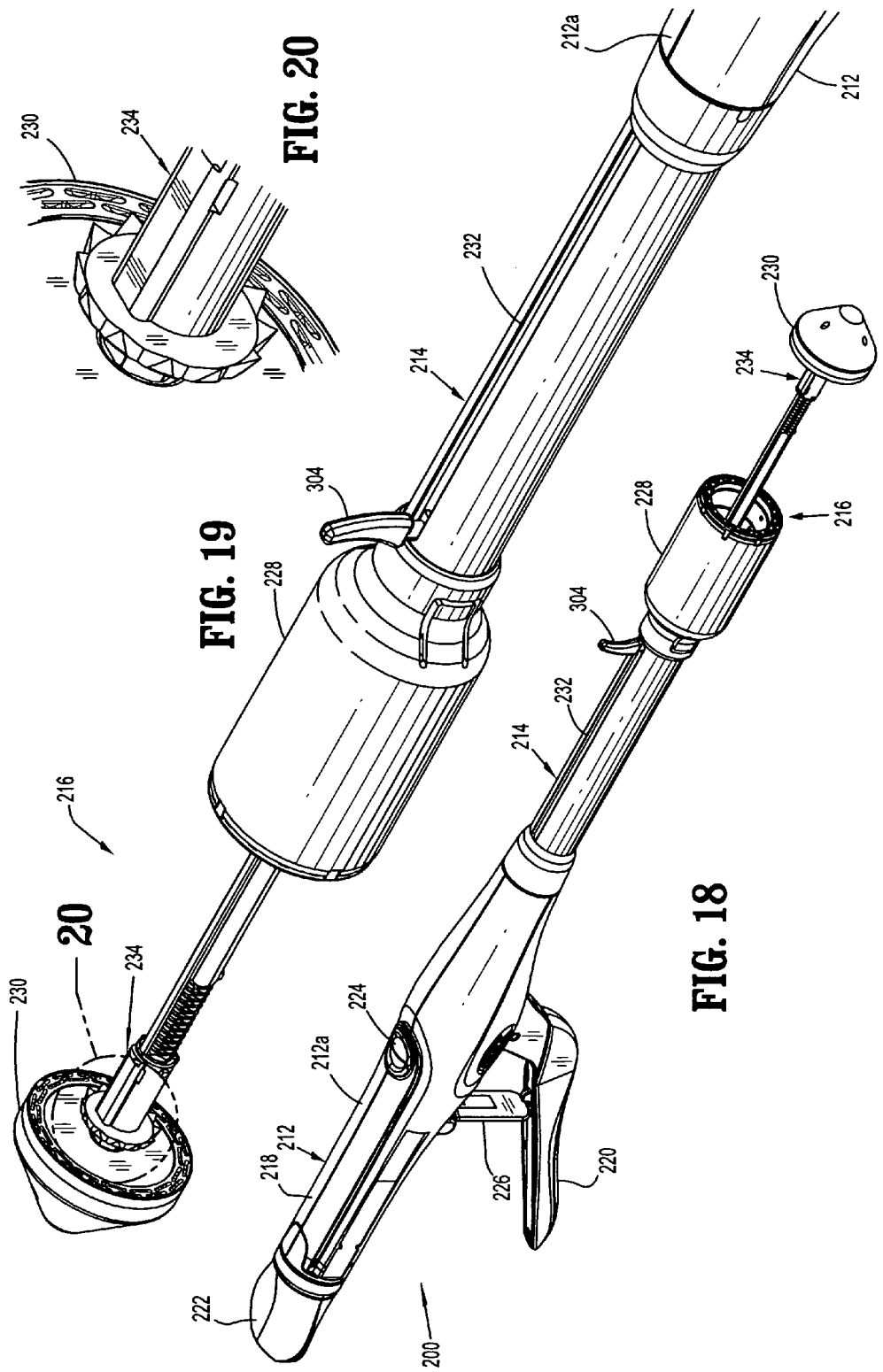

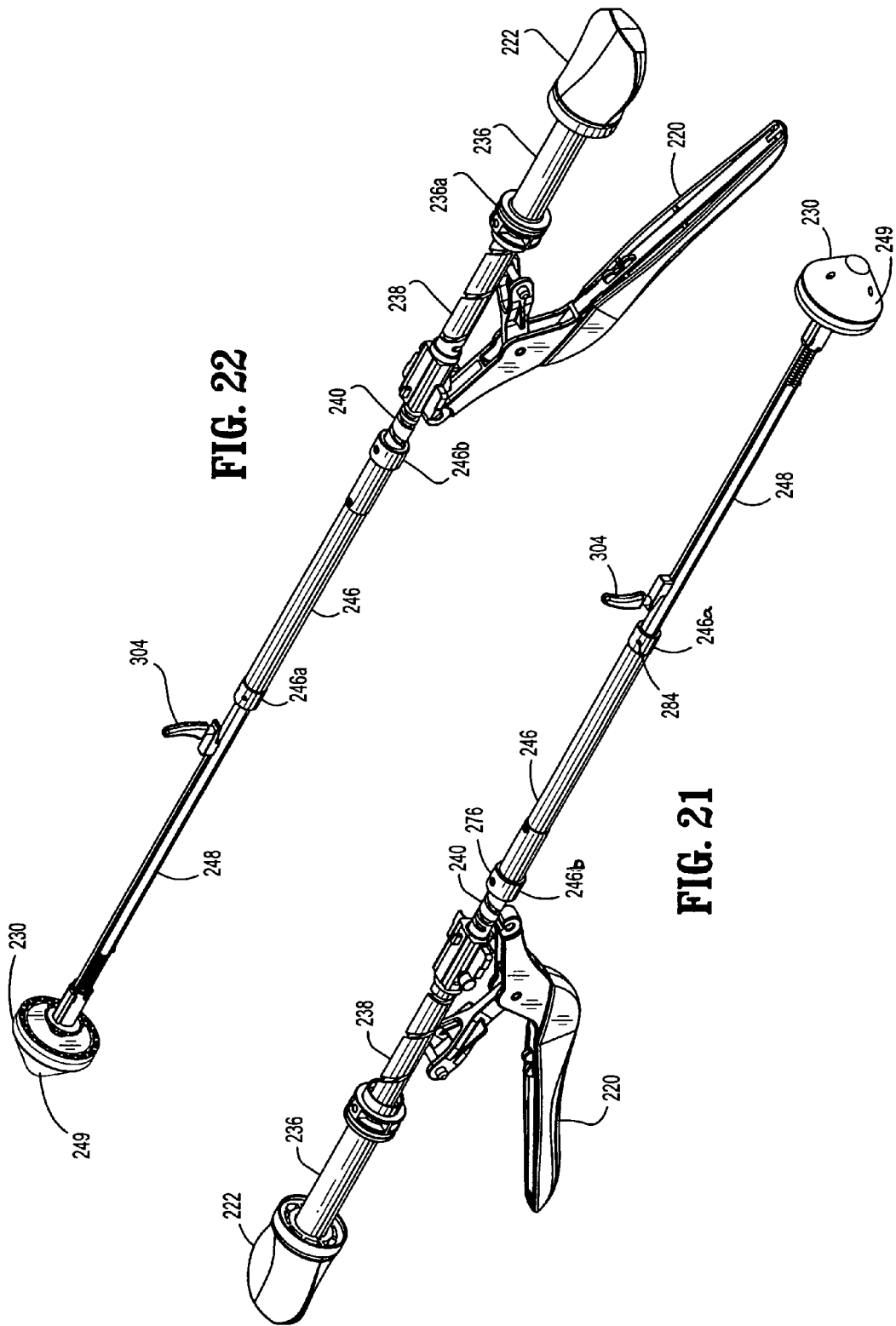

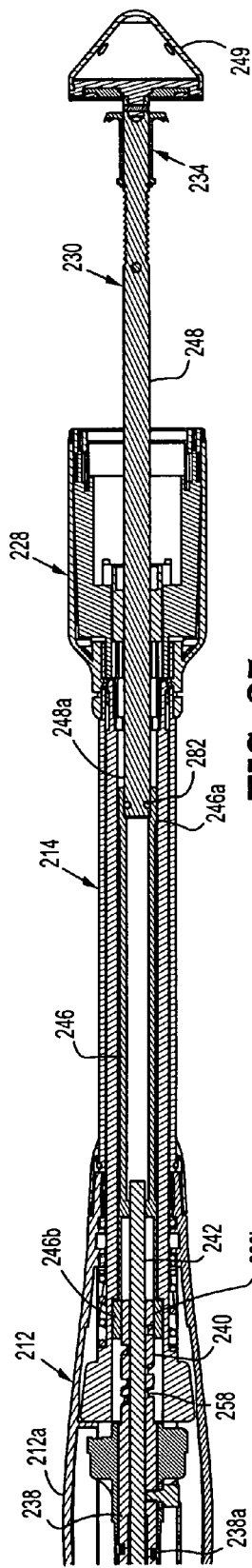
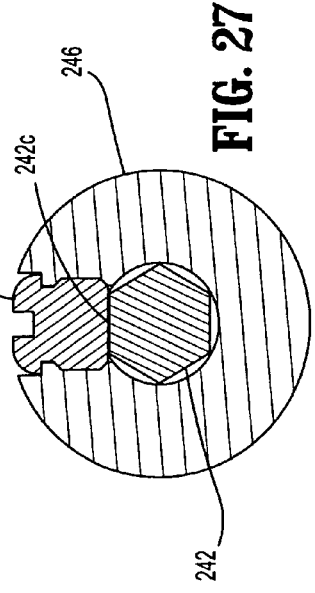
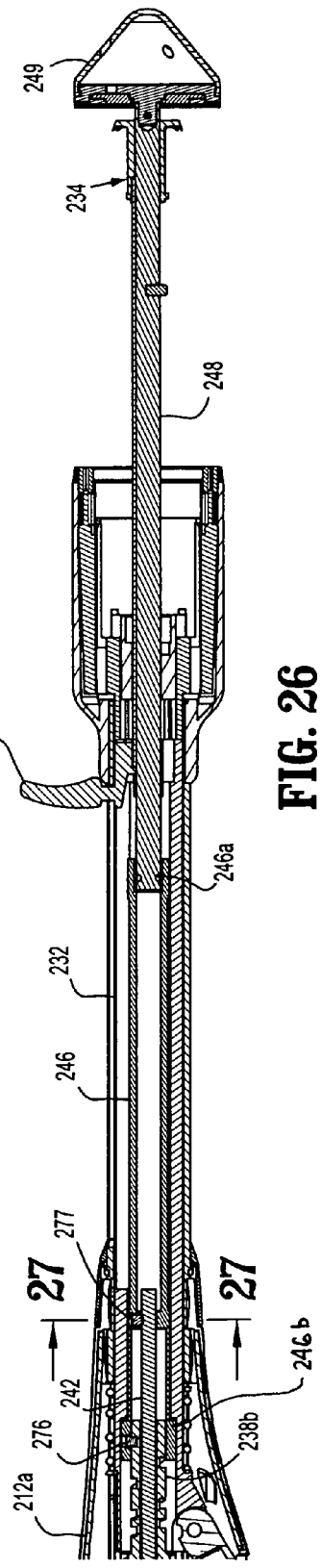
FIG. 25
FIG. 27
FIG. 26

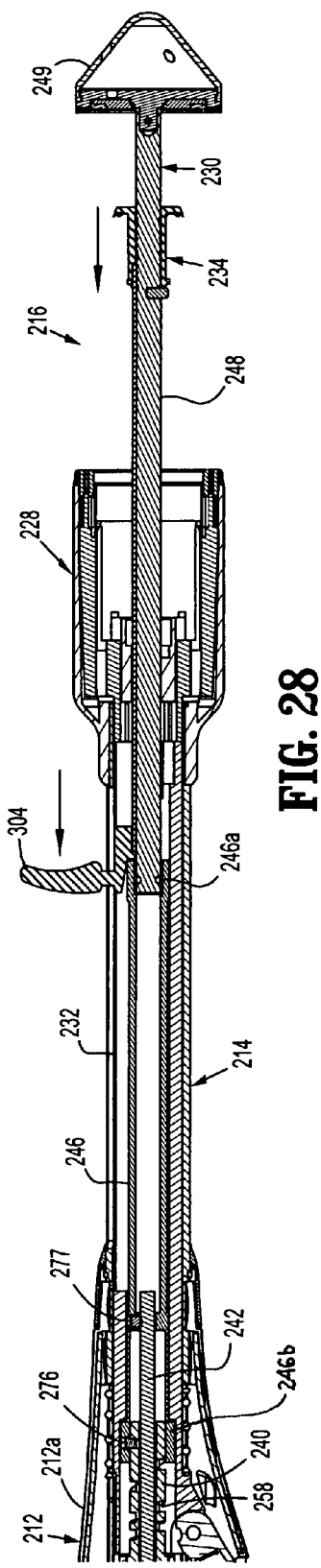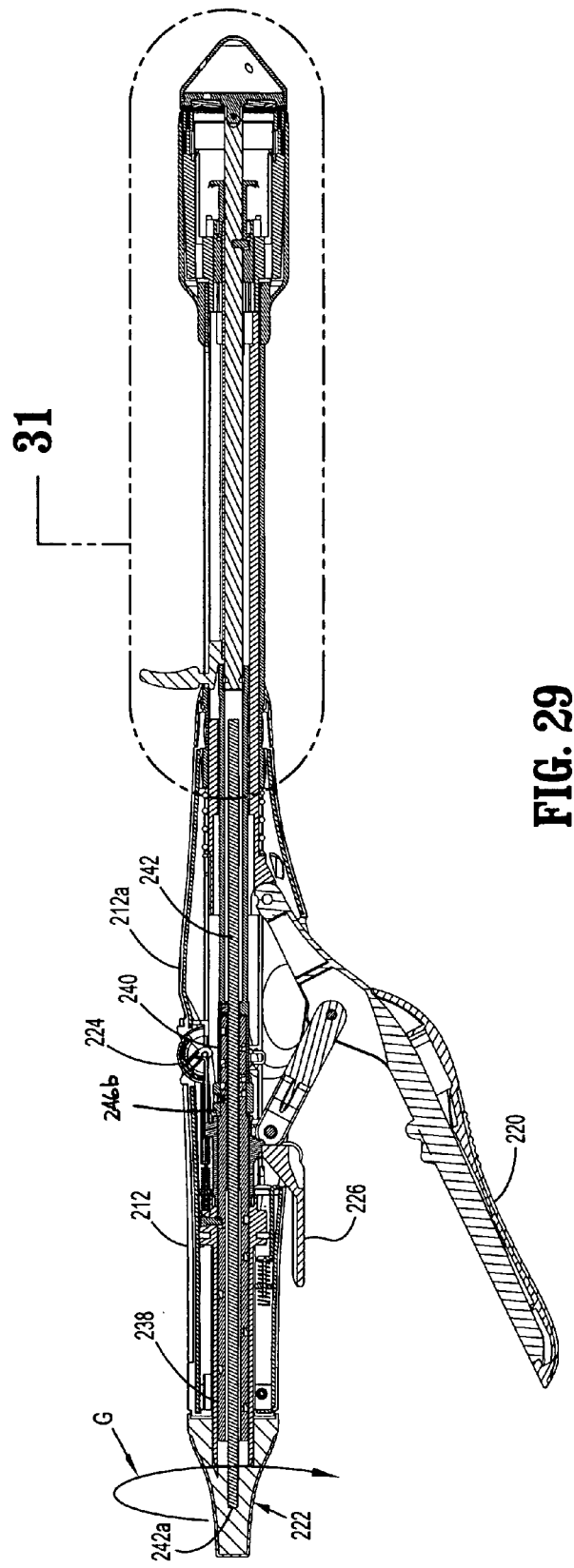
FIG. 28
FIG. 29

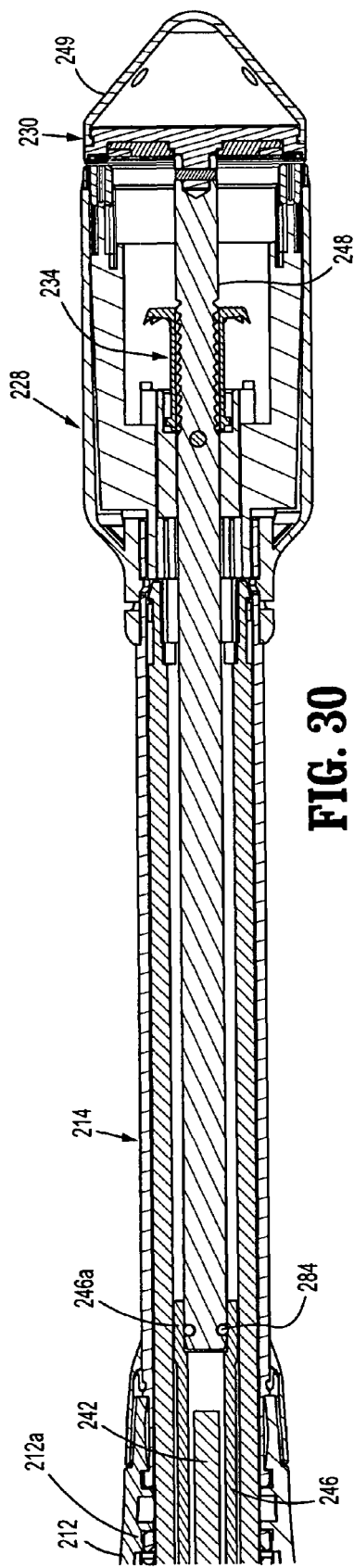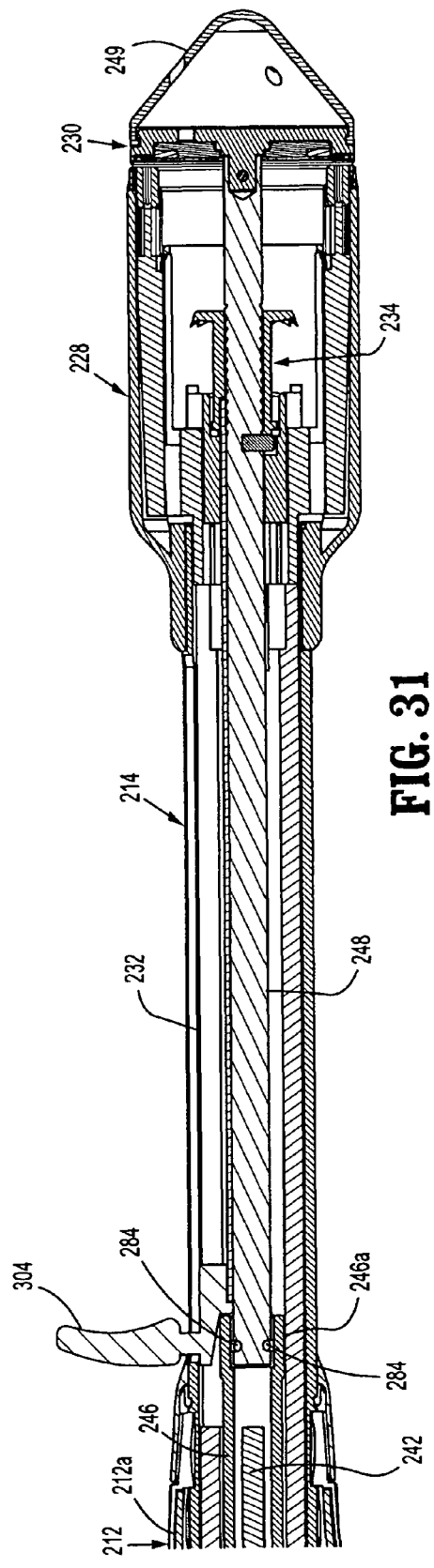

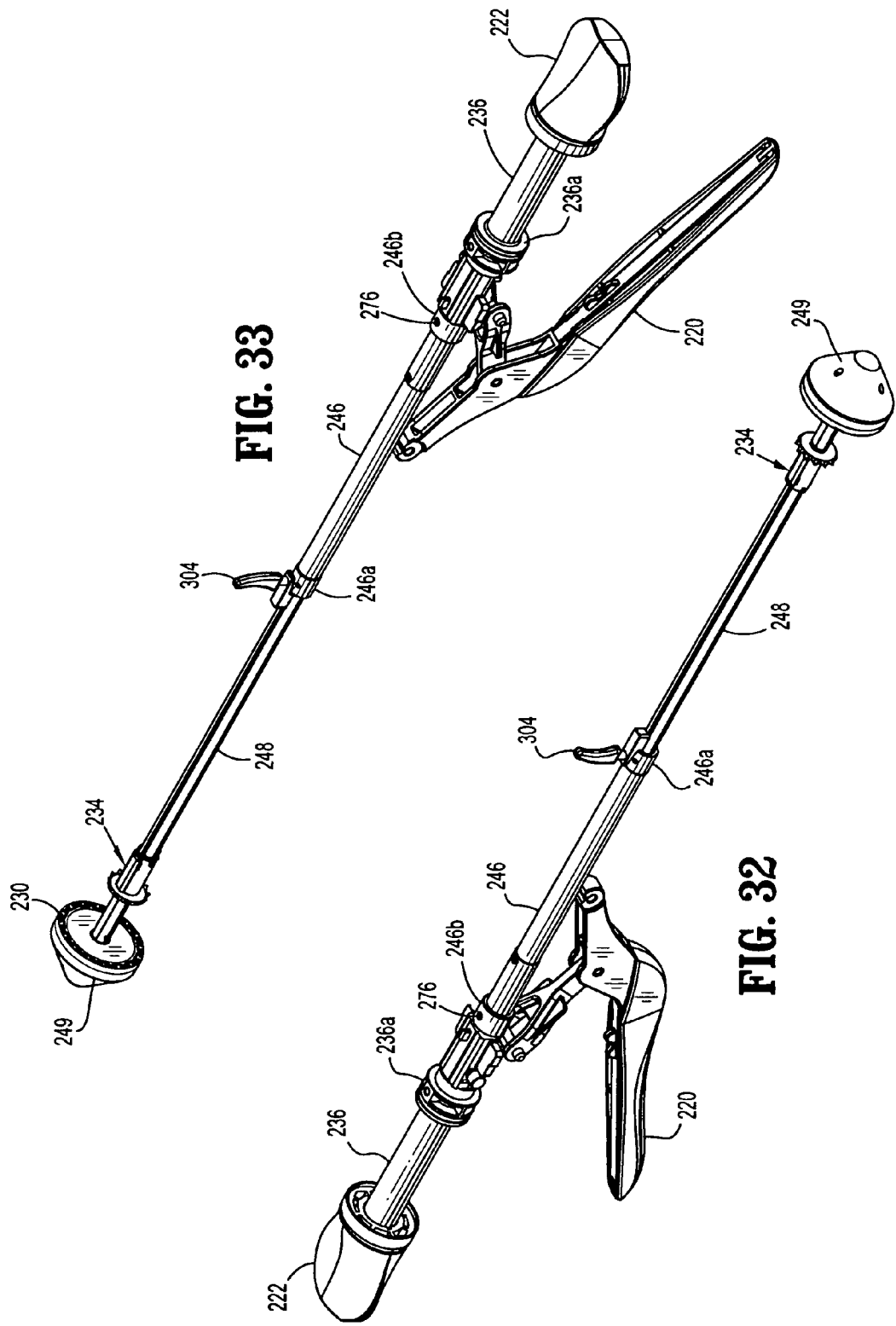

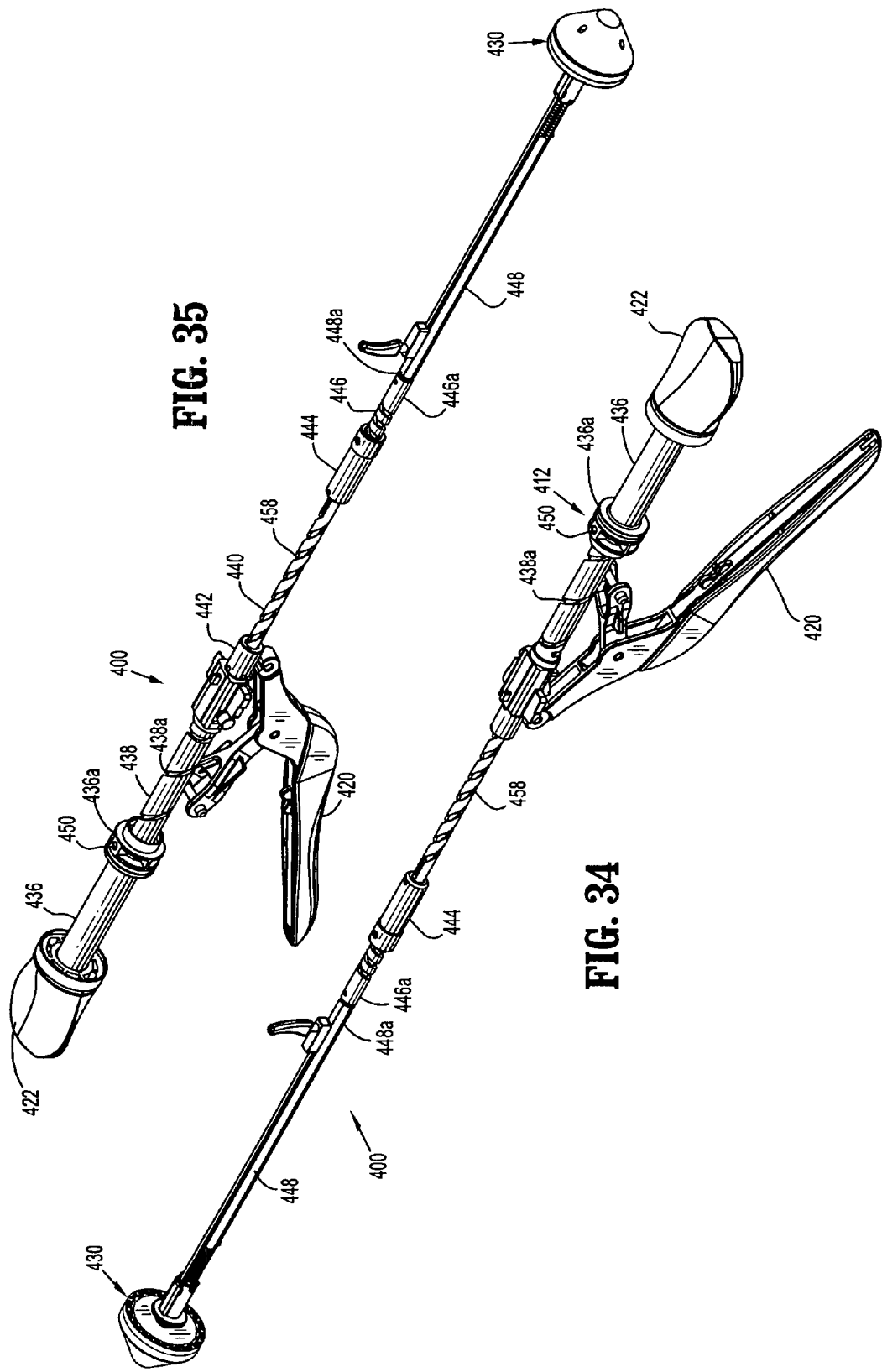

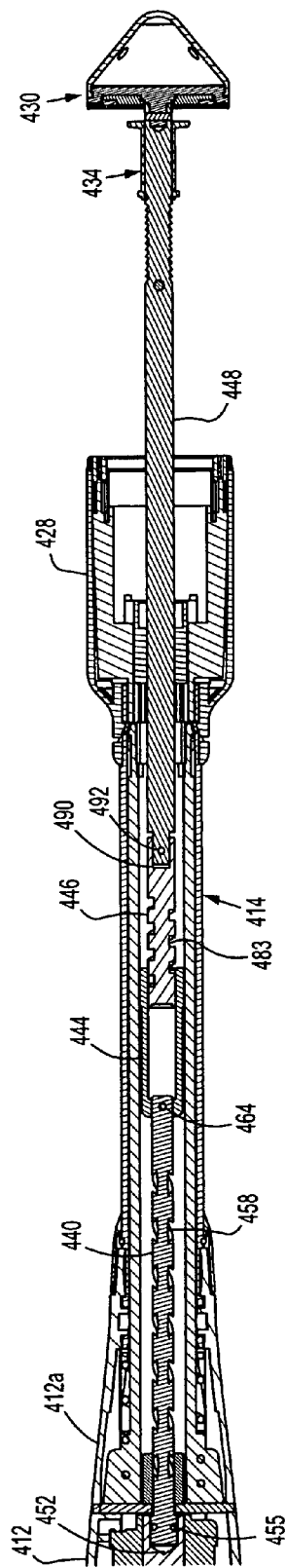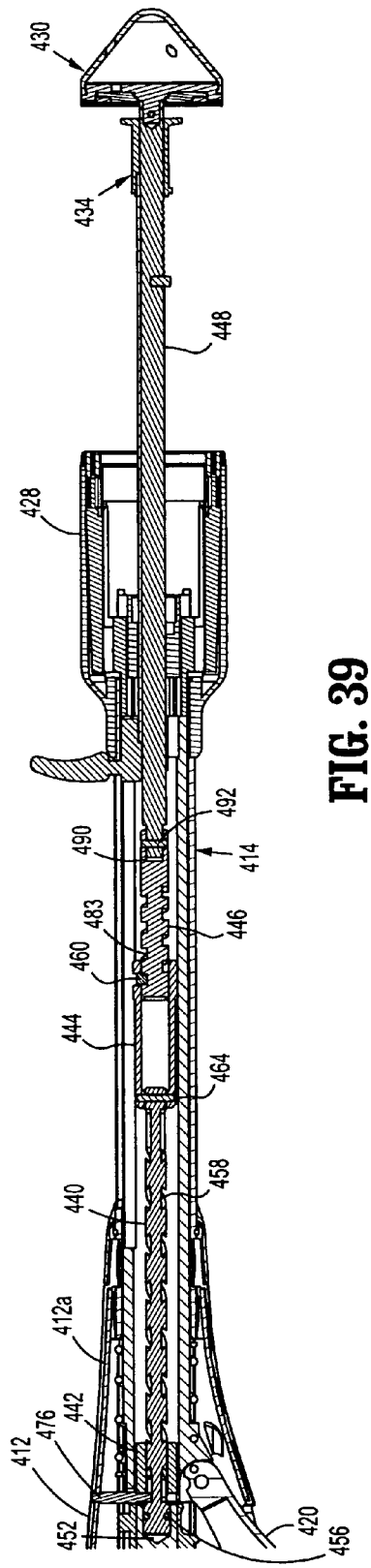

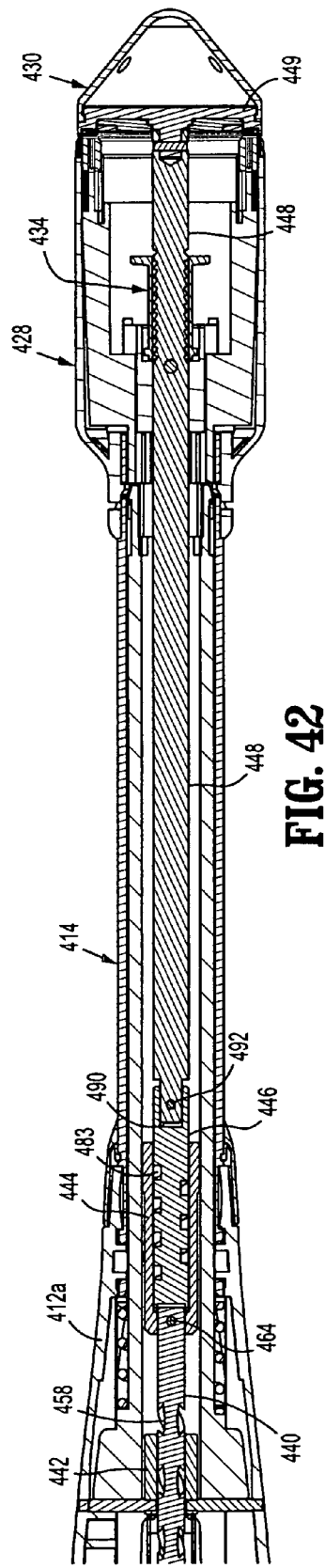
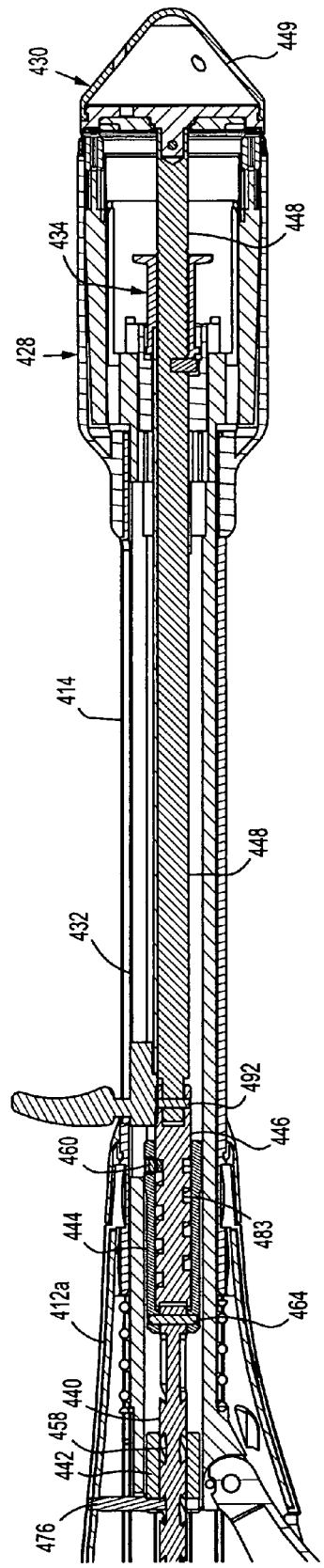
FIG. 42
FIG. 43

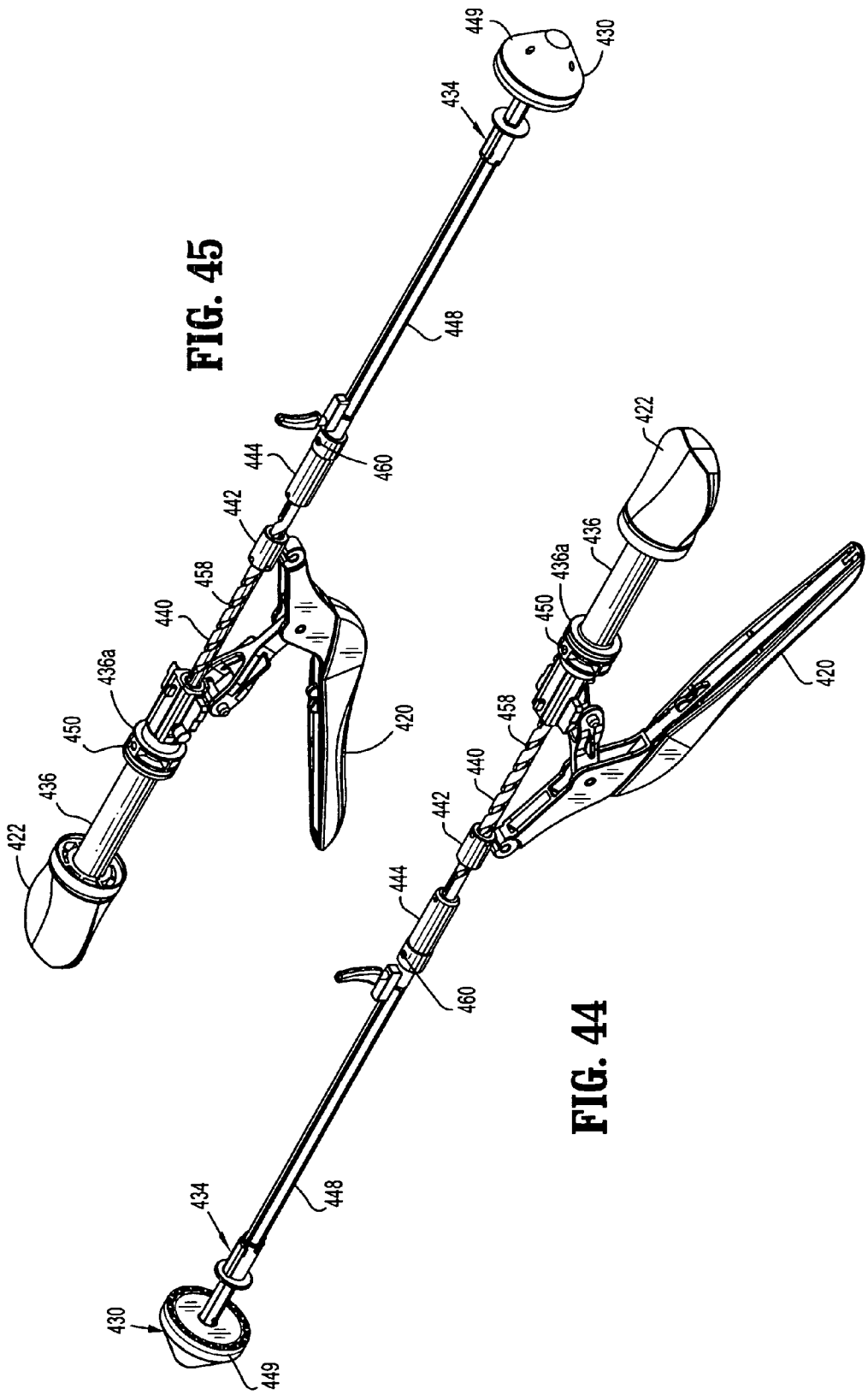

TISSUE TENSIONER ASSEMBLY AND APPROXIMATION MECHANISM FOR SURGICAL STAPLING DEVICE

This application claims priority from U.S. Provisional Application Ser. No. 60/554,556, filed Mar. 19, 2004, and from U.S. Provisional Application Ser. No. 60/554,562, filed Mar. 19, 2004, the contents of which are incorporated by reference in their entirety.

BACKGROUND

1. Technical Field

The present disclosure relates generally to a surgical stapling device for treating hollow tissue organs. More particularly, the present disclosure relates to a surgical stapling device having an approximation mechanism.

2. Background of the Related Art

Anastomosis is the surgical joining of separate hollow organ sections. Typically, an anastomosis procedure follows surgery in which a diseased or defective section of hollow tissue is removed and the remaining end sections are joined. Depending on the desired anastomosis procedure, the end sections may be joined by either circular, end-to-end or side-to-side organ reconstruction methods.

In a known circular anastomosis procedure, two ends of organ sections are joined by means of a stapling device which drives a circular array of staples through the end of each organ section and simultaneously cores any tissue interior of the driven circular array of staples to free a tubular passage. Examples of devices for performing circular anastomosis of hollow organs are described in U.S. Pat. Nos. 6,053,390, 5,588,579, 5,119,983, 5,005,749, 4,646,745, 4,576,167, and 4,473,077, each of which is incorporated herein in its entirety by reference. Typically, these devices include an elongated shaft having a handle portion at a proximal end thereof to effect actuation of the device and a staple holding component disposed at a distal end thereof. An anvil assembly including an anvil shaft with attached anvil head is mounted to the distal end of the device adjacent a staple holding component. Opposed end portions of tissue of the hollow organ(s) to be stapled are clamped between the anvil head and the staple holding component of the device. The clamped tissue is stapled by driving one or more staples from the staple holding component so that the ends of the staples pass through the tissue and are deformed by the anvil head. An annular knife is concurrently advanced to core tissue within the hollow organ to free a tubular passage within the organ.

Surgical stapling devices for performing circular anastomosis have also been used to treat internal hemorrhoids in the rectum. During the use of a circular stapling device for hemorrhoid treatment, the anvil head and the staple holding component of the surgical stapling device are inserted through the anus and into the rectum with the anvil head and the staple holding component in an open or unapproximated position. Thereafter, a purse string suture is used to pull the internal hemorrhoidal tissue and/or mucosal tissue towards the anvil rod. Next, the anvil head and the staple holding component are approximated to clamp the hemorrhoidal tissue and/or mucosal tissue between the anvil head and the staple holding component. The stapling device is fired to remove the hemorrhoidal tissue and/or mucosal tissue and staple the cut tissue.

Despite its success and the overall acceptance of its many benefits, the use of circular anastomosis staplers presents a number of challenges. In particular, due to the close proximity of anvil head to the staple holding component, visibility of access to the surgical site is limited, especially during procedures for the treatment of hemorrhoids. Moreover, during approximation of the anvil head and staple holding component of the surgical stapling device, it is sometimes difficult to properly position tissue to be removed within the staple holding component of the surgical stapling device. As such, the tissue may bunch up in a tissue gap defined between the anvil head and the staple holding component of the instrument. This may result in malformed staples and/or ineffective removal of all the desired tissue.

Accordingly, a continuing need exists in the art for a circular stapling device for the treatment of tissue which can provide for improved visibility and access to a surgical site. Moreover, a continuing need exists in the art for a circular stapling device for the treatment of tissue which can quickly and easily position tissue to be removed within the staple holding component of the surgical stapling device.

SUMMARY

In accordance with the present disclosure, a surgical stapling device for treating hollow tissue organs is disclosed. The surgical stapling device includes a handle assembly, an elongated body portion, a distal head portion and an approximation mechanism. The elongated body portion extends distally from the handle assembly. The distal head portion is supported on a distal end of the elongated body portion and includes an anvil assembly and a shell assembly. The shell assembly supports a plurality of staples. The anvil assembly includes an anvil head assembly and an anvil shaft. The anvil assembly is movable in relation to the shell assembly between spaced and approximated positions.

The approximation mechanism includes a rotatable approximation knob, a drive member and an extension mechanism. The approximation knob is operably connected to the drive member and is actuable to effect axial movement of the drive member over a first distance. The extension mechanism is operably connected to the drive member and to the anvil shaft such that axial movement of the drive member over the first distance effects axial movement of the anvil shaft in relation to the drive member over a second distance.

In one embodiment, the extension mechanism includes an elongated drive shaft having a proximal end fixedly connected to the approximation knob and a distal end rotatably fixed to a tubular extender, such that rotation of the approximation knob effects rotation of the drive shaft and the tubular extender. The distal end of the tubular extender is operably connected to the anvil shaft and the drive member includes a longitudinal bore. The drive shaft extends from the approximation knob to the tubular extender through the longitudinal bore. The drive member includes a distal extension having a helical groove formed thereabout. The tubular extender includes a cam member positioned within the helical groove. Actuation of the approximation knob effects rotation of the tubular extender about the distal extension of the drive member such that the tubular extender cam member moves in relation to the helical groove. Movement of the cam member in relation to the helical groove effects axial movement of the tubular member in relation to the drive member over the second distance.

In one embodiment, the tubular extender is rotatably connected to the proximal end of the anvil shaft. The elongated drive shaft may include at least one flat surface and the tubular extender may include a set screw for rotatably fixing the tubular extender to the drive shaft.

In another embodiment, the extension mechanism includes an extension sleeve having a cam member supported thereon.

An extender is fixedly attached to a proximal end of the anvil shaft. A drive member extension is rotatably coupled to the distal end of the drive member and includes a distal end fixedly secured to the extension sleeve. The drive member extension includes a first helical groove which is dimensioned to receive a pin which is fixedly secured to the stapling device such that axial movement of the drive member extension in relation to the pin effects rotation of the drive member extension and the extension sleeve in relation to the drive member. The extender includes a second helical groove which is dimensioned to receive a cam member supported on the extension sleeve. When the extension sleeve is rotated in relation to the extender, the extender and the anvil shaft are moved axially in relation to the drive member over the second distance.

In another embodiment, the stapling device includes a tissue tensioner assembly which includes a tissue engaging member slidably positioned on the anvil shaft, an elongated link and an actuator member. The elongated link connects the actuator member to the tissue engaging member. In one embodiment, the tissue engaging member includes a locking member for releasably engaging a series of axially spaced teeth positioned on the anvil shaft to releasably secure the tissue engaging member at one of a plurality of fixed axial locations along the anvil shaft.

In one embodiment, the locking member includes a spring detent and the tissue engaging member includes a hollow body which is slidably positioned about the anvil shaft. The anvil shaft and the hollow body may be shaped to prevent rotation of the hollow body about the anvil shaft, e.g., the hollow body may define a hexagonal bore and the anvil shaft may have a hexagonal cross-section.

Other features and advantages of the present disclosure will become apparent from the following detailed description, taken in conjunction with the accompanying drawings, which illustrate, by way of example, the principals of the invention.

BRIEF DESCRIPTION OF THE DRAWINGS

The foregoing features of the presently disclosed surgical stapling device will become more readily apparent and will be better understood by referring to the following detailed description of embodiments, which are described hereinbelow with reference to the drawings wherein:

FIG. 1 is a perspective view of one embodiment of the surgical stapling device constructed in accordance with the principles of the present disclosure;

FIG. 2 is a perspective view of the distal portion of the surgical stapling device shown in FIG. 1;

FIG. 3 is an enlarged view of the indicated area of detail shown in FIG. 2;

FIGS. 2a-2b are perspective views of the approximation mechanism of the surgical stapling device shown in FIG. 1;

FIG. 9 is a cross-sectional view of the surgical stapling device shown in FIG. 1 taken along section line 9-9 shown in FIG. 8;

FIG. 10 is an enlarged view of the indicated area of detail shown in FIG. 8;

FIG. 9a is a perspective view of the distal end of the surgical stapling device shown in FIG. 1 positioned adjacent a lumen of a vessel with a purse-string suture applied to a portion of the vessel, the anvil assembly in its unapproximated position and the tissue tensioner assembly in its advanced position;

FIG. 10a is a perspective view of the distal end of the surgical stapling device shown in FIG. 1 positioned adjacent a lumen of a vessel with the purse-string suture cinched about the tissue tensioner shaft, the anvil assembly in its unapproximated position and the tissue tensioner device in its advanced position;

FIG. 10d is an enlarged view of the indicated area of detail show in FIG. 10;

FIG. 11 is a perspective view of the surgical stapling device shown in FIG. 1, illustrating the anvil assembly in its approximated position and the tissue tensioner assembly in a fully retracted position;

FIG. 12 is a perspective view of the distal end of the surgical stapling device shown in FIG. 1, the anvil assembly in its approximated position and the tissue tensioner assembly in a fully retracted position;

FIG. 13 is an enlarged view of the indicated are of detail shown in FIG. 13a;

FIG. 14 is an enlarged view of the indicated are of detail shown in FIG. 14a;

FIG. 16 is a cross-sectional view taken along section line 16-16 shown in FIG. 15;

FIG. 17 is an enlarged view of the indicated area of detail shown in FIG. 15;

FIG. 18 is a perspective view of another embodiment of the surgical stapling device constructed in accordance with the principles of the present disclosure;

FIG. 19 is a perspective view of the distal portion of the surgical stapling device shown in FIG. 18;

FIG. 20 is an enlarged view of the indicated area of detail show in FIG. 19;

FIGS. 21-22 are perspective views of the approximation mechanism of the surgical stapling device shown in FIG. 18;

FIG. 25 is a cross-sectional view taken along section line 25-25 shown in FIG. 24;

FIG. 26 is an enlarged view of the indicated are of detail shown in FIG. 24;

FIG. 27 is a cross-sectional view taken along section line 27-27 shown in FIG. 26;

FIG. 28 is a side cross-sectional view of the distal end of the surgical stapling device shown in FIG. 18 illustrating actuation of the tissue tensioner assembly to a retracted position;

FIG. 29 is a side cross-sectional view of the surgical stapling device shown in FIG. 18 illustrating rotation of the rotatable approximation to approximate the anvil assembly;

FIG. 30 is a top cross-sectional view of the distal portion of the surgical stapling device shown in FIG. 18, the anvil assembly in its approximated position and the tissue tensioner assembly in a fully retracted position;

FIG. 31 is an enlarged view of the indicated are of detail shown in FIG. 29;

FIGS. 32-33 are perspective views of the approximation mechanism of the surgical stapling device shown in FIG. 18, illustrating the anvil assembly in its approximated position and the tissue tensioner device in a retracted position;

FIGS. 34-35 are perspective views of another embodiment of the approximation mechanism constructed in accordance with the principles of the present disclosure;

FIG. 38 is a top cross-sectional view of the distal portion of the surgical stapling device shown in FIG. 37;

FIG. 39 is an enlarged view of the indicated are of detail shown in FIG. 37;

FIG. 42 is a top cross-sectional view of the distal portion of the surgical stapling device shown in FIG. 41;

FIG. 43 is an enlarged view of the indicated area of detail shown in FIG. 41; and FIGS. 44-45 are perspective views of the approximation mechanism shown in FIG. 34, illustrating the anvil assembly in its approximated position and the tissue tensioner device in a retracted position.

DETAILED DESCRIPTION OF EMBODIMENTS

Figure 4:
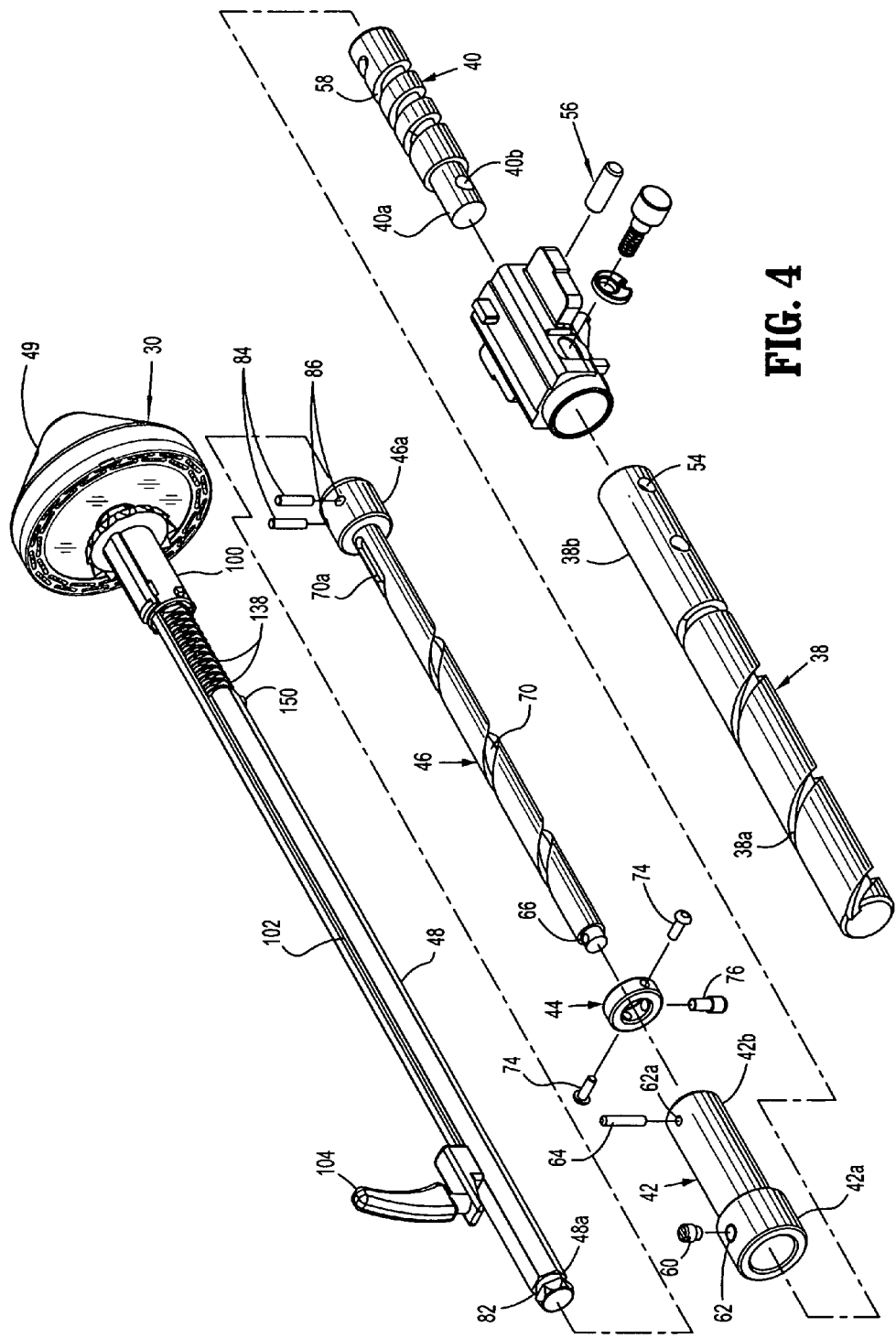
FIG. 4 is a perspective view, with parts separated, of the approximation mechanism of the surgical stapling device shown in FIG. 1.

Embodiments of the presently disclosed surgical stapling device will now be described in detail with reference to the drawings wherein like reference numerals designate identical or corresponding elements in each of the several views.

Throughout this description, the term "proximal" will refer to the portion of the device closest to the operator and the term "distal" will refer to the portion of the device furthest from the operator. Although this description focuses primarily on surgical staplers, it is envisioned that the benefits of what is disclosed herein may also be realized in other fastener applying devices including two part fastener applying devices and energy assisted tissue sealing devices, e.g., radio frequency ("RF") tissue sealing devices.

FIGS. 1-3 illustrate one embodiment of the presently disclosed surgical stapling device which is shown generally as 10. Briefly, surgical stapling device 10 includes a handle assembly 12, an elongated body portion 14, a distal head portion 16 and a tissue tensioner assembly 34. Although elongated body portion 14 is shown as being substantially straight, it is contemplated, as is known in the art, to provide a curved body portion.

Handle assembly 12 includes a stationary housing 12a defining a grip 18, a firing trigger 20, a rotatable approximation knob 22, a firing indicator 24 and a firing trigger lockout 26. Each of these components functions substantially as described in U.S. Provisional Application Ser. No. 60/480, 074, entitled "Surgical Stapling Device" and filed on Jun. 20, 2003, and U.S. Provisional Application Ser. No. 60/487,841, entitled "Surgical Stapling Device With Tissue Tensioner" and filed on Jul. 16, 2003, and will not be discussed in detail herein. Each of these applications is incorporated herein in its entirety by reference.

Head portion 16 includes a shell assembly 28 and an anvil assembly 30. Shell assembly 28 is secured to a distal end of elongated body portion 14. Elongated body portion 14 includes an elongated slot 32 for slidably receiving a tensioner actuation member 104 of tissue tensioner assembly 34 which will be described in further detail below.

Handle assembly 12 includes the proximal components of the approximation and firing mechanisms of device 10, a firing lockout mechanism and an indicator mechanism. The firing mechanism, the firing lockout mechanism and the indicator mechanism are substantially as described in the '074 and '841 applications and will not be described in detail herein. The approximation mechanism of device 10 has been modified from that described in the '074 and '841 applications to provide better visibility of and improved access to the surgical site. These modifications will now be discussed.

Referring to FIGS. 2a, 2b, 4 and 8-10, the approximation mechanism includes rotatable approximation knob 22 (FIGS. 2a and 2b), a rotatable sleeve 36, a drive screw 38, a screw extension 40, an extension sleeve 42, a pin support member 44 and an extender shaft 46. As shown in FIG. 4, the distal end 46a of extender shaft 46 is rotatably coupled to a proximal end 48a of anvil shaft 48 of anvil assembly 30. When approximation knob 22 is rotated or actuated, anvil assembly 30 is moved in relation to shell assembly 28 (FIG. 1) between spaced and approximated positions in a manner described in detail below.

Approximation knob 22 is secured to the proximal end of rotatable sleeve 36 using any known fastening technique, e.g., pin(s), adhesives, key/slot arrangement, welding, etc. The distal end 36a of rotatable sleeve 36 is rotatably secured within handle assembly housing 12a (FIG. 1) in the manner described in the '074 application. A pin 50 (FIG. 8) extends through distal end 36a of rotatable sleeve 36 and is received within a helical groove 38a of drive screw 38. When sleeve 36 is rotated by rotating approximation knob 22, pin 50 moves within helical groove 38a to move drive screw 38 axially within housing 12a of handle assembly 12. Helical groove 38a has a pitch of between about 0.09 thousandths of an inch/revolution to about 0.90 thousandths of an inch/revolution.

The distal end 38b (FIG. 4) of drive screw 38 includes an axial bore 52 (FIG. 8) and a transverse throughbore 54 (FIG. 4). The proximal end of screw extension 40 includes a reduced diameter portion 40a having a transverse bore or opening 40b. A pin or coupling member 56 extends through throughbores 54 and 40b of drive screw 38 and screw extension 40, respectively, to fixedly secure screw extension 40 to distal end 38b of drive screw 38. When drive screw 38 is moved axially by rotating approximation knob 22, this movement is translated to axial movement of screw extension 40. It is envisioned that drive screw 38 and screw extension 40 may be integrally or monolithically formed.

The outer surface of screw extension 40 includes a helical channel 58. In one embodiment, helical channel 58 has a pitch of between about 0.06 thousandths of an inch/revolution and about 0.40 thousandths/revolution and, in a particularly useful embodiment, channel 58 has a pitch of between about 0.120 thousandths of an inch/revolution to about 0.330 thousandths of an inch/revolution. Extension sleeve 42 is tubular and is slidably positioned about screw extension 40. A pin or cam member 60 extends through a bore or opening 62 formed in a proximal end 42a of extension sleeve 42. Pin 60 is slidably positioned within helical channel 58 of screw extension 40 such that when screw extension 40 is moved axially in response to rotation of approximation knob 22, extension sleeve 42 is rotated about and moves axially over screw extension 40 as pin 60 moves through helical channel 58.

The distal end 42b of extension sleeve 42 includes a transverse bore or opening 62a for receiving a pin or coupling member 64. Pin 64 is received within a throughbore 66 formed in the proximal end of extender shaft 46 to rotatably and axially secure extension sleeve 42 to extender shaft 46. When approximation knob 22 is rotated to move drive screw 38 and screw extension 40 axially and to rotate and axially move extension sleeve 42 about screw extension 40, extender shaft 46 is also rotated about its longitudinal axis and moved axially with extension sleeve 42.

Extender shaft 46 includes a helical groove 70 formed about its exterior surface. In one embodiment, the helical groove 70 has a pitch of between about 0.50 thousandths of an inch/revolution to about 0.85 thousandths of an inch/revolution. In a particularly useful embodiment the pitch of helical groove 70 is 0.836 thousandths of an inch/revolution. A pin support member 44 is fixedly secured to a pusher 72 (FIGS. 9 and 10) of device 10. Pin support member 44 is supported about extender shaft 46 by a pair of pins or screws 74. Pusher 72 and pin support member 44 remain at a fixed location within body portion 14 during approximation of device 10. A pin or cam member 76 extends through pin support member 44 into helical groove 70 of extender shaft 46. When extender shaft 46 is rotated by extension sleeve 42, movement of helical groove 70 in relation to fixed pin 76 effects axial movement of extension sleeve 42 and extender shaft 46 in relation to drive screw 38 and screw extension 40.

Figure 14A:
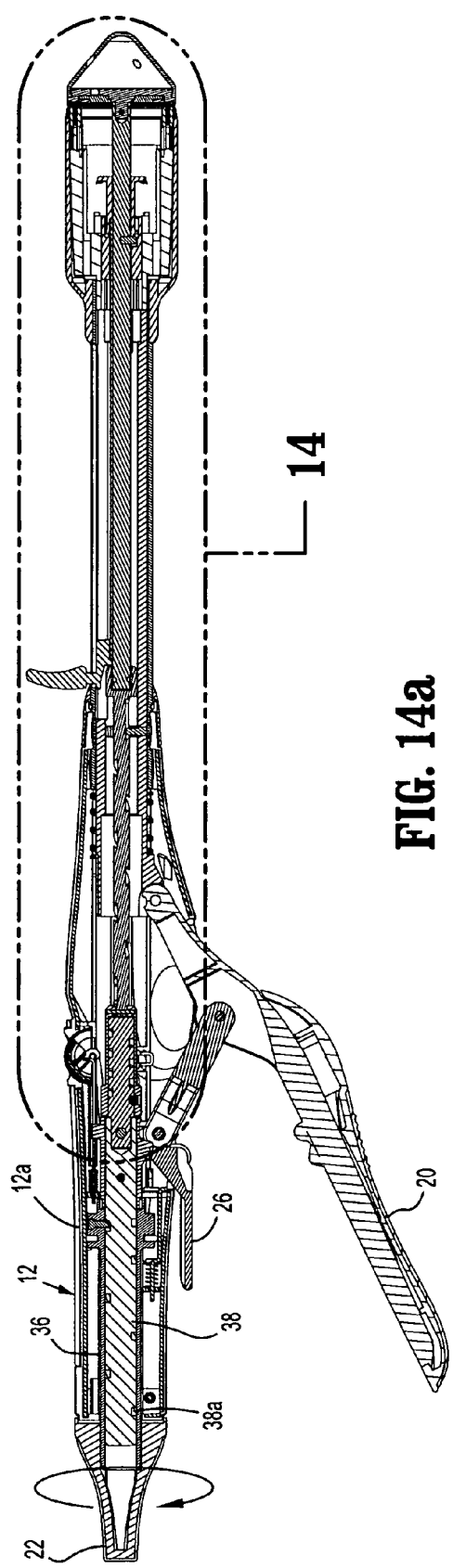
FIG. 14a is a side cross-sectional view of the surgical stapling device shown in FIG. 1 illustrating rotation of the rotatable approximation knob to approximate the anvil assembly.

As illustrated in FIG. 4, the distal end of helical groove 70 includes a linear section 70a. When extender shaft 46 is in its proximal-most or retracted position (FIG. 14), pin 76 is positioned in linear section 70a of helical groove 70. Thus, when pusher 72 is actuated to eject staples from shell assembly 28, in the manner described in detail in the '074 and '841 applications, pin 76 moves freely through linear section 70a of helical groove 70 without effecting further movement of extender shaft 46.

The distal end of extender shaft 46 includes a hub portion 46a defining an axial bore 80 (FIG. 9) for receiving a proximal end of anvil shaft 48 of anvil assembly 30. The proximal end 48a of anvil shaft 48 includes an annular channel 82. A pair of pins 84 extend through openings 86 formed in hub portion 46a of extender shaft 46 through a portion of annular channel 82 to axially fix and rotatably secure extender shaft 46 to anvil shaft 48.

Figure 5:
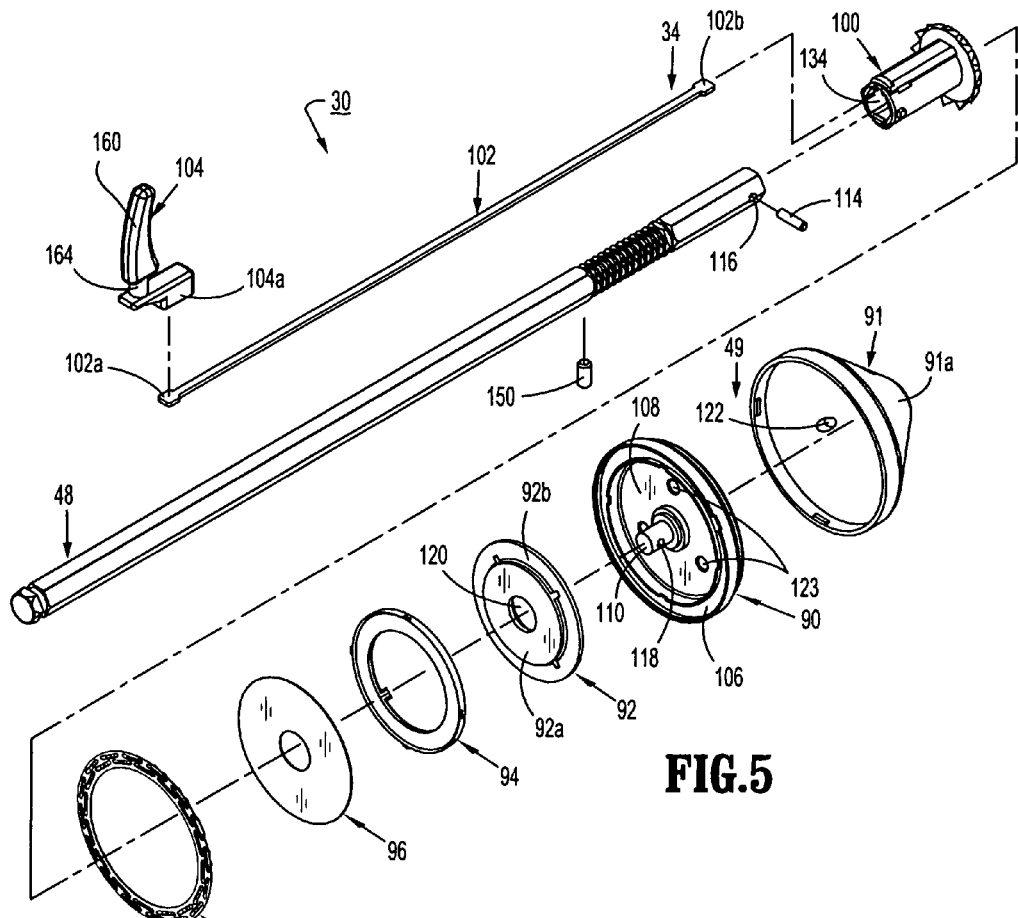
FIG. 5 is a perspective view, with parts separated, of the anvil assembly and the tissue tensioner assembly of the surgical stapling device shown in FIG. 1.

Referring to FIG. 5, anvil assembly 30 includes anvil shaft 48 and an anvil head assembly 49 including anvil body 90, an anvil cover 91, a backup plate 92, a cutting ring 94, a cutting ring cover 96, and an anvil plate 98. In one embodiment, anvil cover 91 includes openings 122 and anvil body 90 includes openings 123 which together define a fluid passage to relieve pressure which may build up within anvil assembly 30. See FIG. 5. Anvil cover 91 is secured to a distal end of anvil body 90 and includes a tapered, blunt distal face 91a which provides smooth entry of anvil head assembly 49 into a body lumen. Anvil cover 91 is secured to anvil body 90 using any known fastening technique including snap-fitting, adhesives, screws, pins, friction, etc.

Anvil body 90 defines an outer annular channel 106 and an inner annular channel 108 and includes a central post 110. Central post 110 is dimensioned to be received within an axial bore 112 (FIG. 9) formed in the distal end of anvil shaft 48. A pin 114 extends through openings or bores 116 and 118 formed in anvil shaft 48 and central post 110, respectively, to fixedly secure anvil shaft 48 to central post 110.

Backup plate 92, cutting ring 94 and cutting ring cover 96 may form an integral assembly. In the alternative, the components may be independent and stacked. In one embodiment, backup plate 92 is formed from a hard material such as steel or other surgically approved metal, and includes a central throughbore 120 which is positioned about central post 110 of anvil body 90. Backup plate 92 includes a raised circular platform 92a and an outer annular ring 92b. Cutting ring 94 is dimensioned to be positioned on outer annular ring 92b of backup plate 92 and may be secured thereto using adhesives or the like. In one embodiment, cutting ring 94 is formed from a relatively soft material such as polyethylene and is molded to backup plate 92.

Cutting ring cover 96 is may be formed from a plurality of layers of material such as disclosed in U.S. provisional application Ser. No. 60/554,564 ("'564 application"), entitled "Anvil Assembly With Improved Cut Ring" and filed on Mar. 19, 2004. The '564 application is incorporated herein in its entirety by reference. As disclosed in the '564 application, cover 96 may include a plurality of layers including a first layer spaced from cutting ring 94 formed from a relatively soft material, e.g., polypropylene, a second layer formed of a relatively hard material, e.g., a polyester such as Mylar® available from DuPont, and a third layer formed of a relatively hard material, e.g., polyester such as Mylar®. Alternately, only one or more layers of a relatively hard material may be provided. The plurality of layers may be fastened together with, for example, an adhesive. Alternately, other fastening techniques may be used to secure the layers together, e.g., welding, fusing, molding, compression, etc. The first layer is soft in relation to the second and third layers to permit penetration by a knife blade of a surgical instrument to enhance cutting of tissue. Although stapling device 10 is not typically intended to cut through staples, certain layers of cover 96 are harder and provide a more rigid support for cutting through staples which may be inadvertently positioned between a knife blade of a surgical stapling device (not shown) and cutting ring cover 96. In one embodiment, the first layer has a thickness in the range of about 0.0005" to about 0.0015". In a particularly useful embodiment, the first layer has a thickness of about 0.001" and second and third layers have thicknesses in the range of about 0.0015" to about 0.0025". In a particularly useful embodiment, the thickness of the second and third layers are about 0.002". In the alternative, other materials having different thicknesses may also be used to construct the different layers of cover 96. Moreover, other material configurations may be used to form the relatively hard material layers(s), e.g., a braided, weaved, woven and non-woven materials.

Anvil plate 98 is secured in outer annular channel 106 of anvil body 90 using any known fastening technique, e.g., welding, brazing, crimping, pins, screws, etc. and includes a plurality of staple deforming pockets such as disclosed in the '074 and '841 applications.

Figure 10B:
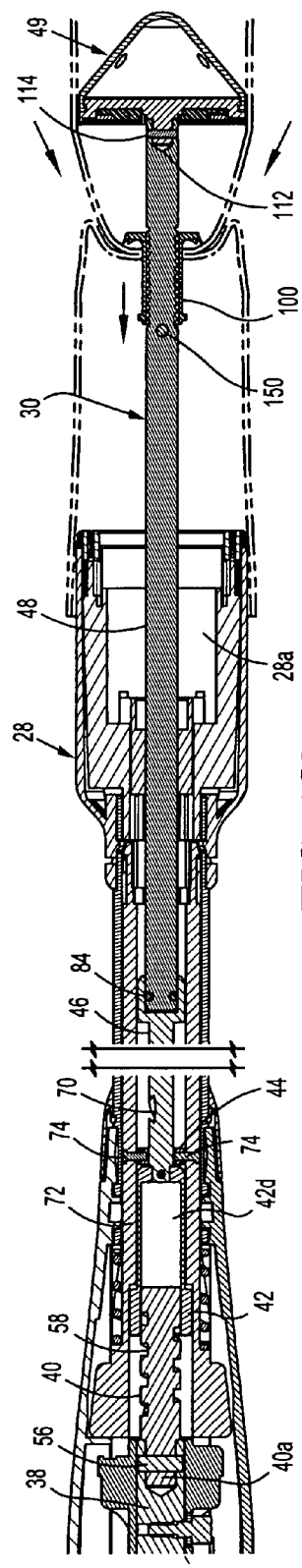
FIG. 10b is a top cross-sectional view of the distal end of the surgical stapling device shown in FIG. 10a positioned adjacent a lumen of a vessel, the anvil assembly in its unapproximated position and the tissue tensioner assembly in a partially retracted position.

Referring to FIGS. 4-7, tissue tensioner assembly 34 is slidably supported on anvil shaft 48 of anvil assembly 30 and includes a tissue tensioner 100, a tensioner link 102 and a tensioner actuator member 104. Tissue tensioner 100 (FIGS. 5-7 and 13) includes a hollow body 130 and a distal head portion 132 defining an opening or throughbore 134 (FIG. 5). Distal head portion 132 may include a plurality of proximally angled projections 132a formed about its periphery (FIG. 3). Projections 132a are configured to engage tissue. In the alternative, head portion 132 may include a smooth surface having no projections. Throughbore 134 may include a non-circular configuration, e.g., a hexagonal configuration which corresponds closely to the cross-section of anvil shaft 48. The hexagonal configuration of throughbore 134 and cross-section of anvil shaft 48 prevent rotation of tensioner 100 in relation to anvil shaft 48 The use of other cross-sections and configurations is contemplated. Tensioner 100 is slidably positioned about anvil shaft 48 and includes a spring detent 136 (FIG. 10d) which is positioned to releasably engage a rack or one of a series of axially spaced teeth 138 to releasably retain tensioner 100 at axially fixed positions along anvil shaft 48. As illustrated in FIG. 10d, each tooth 138 has a distal face 138a and a proximal face 138b. In one embodiment, distal face 138a defines a greater angle α with respect to a vertical axis than angle β defined by the proximal face. In a particularly useful embodiment, angle α is between about 45° and about 75° and angle β is between about 15° and about 45°. In another embodiment, angle α is about 60° and angle β is about 30°. The angles α and β allow for tensioner 100 to move along anvil shaft 48 more easily in a proximal direction.

Figure 6:
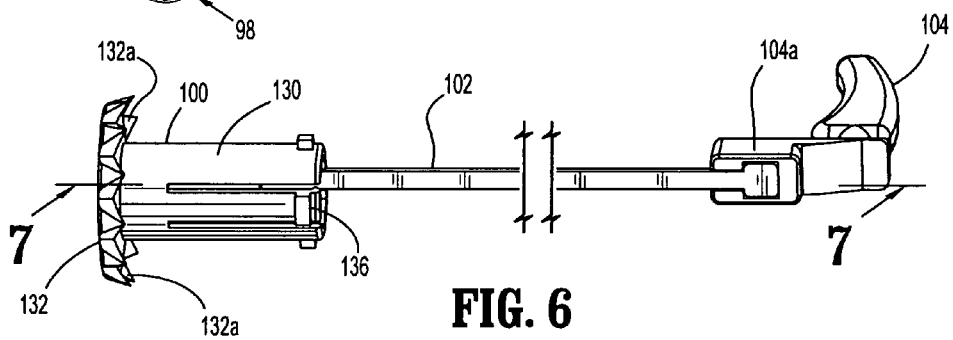
FIG. 6 is a side view of the tissue tensioner assembly of the surgical stapling device shown in FIG. 1.
Figure 7:
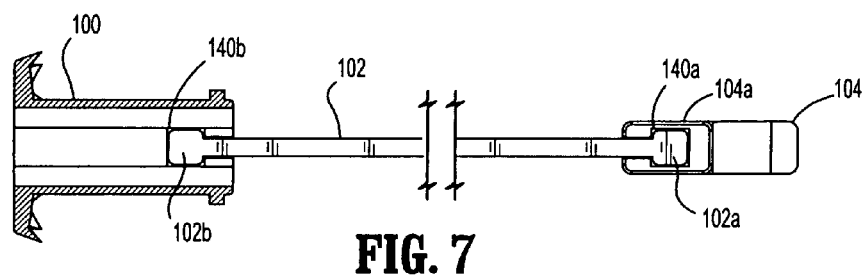
FIG. 7 is a cross-sectional view of the tissue tensioner device taken along section line 7-7 shown in FIG. 6.
Figure 8:
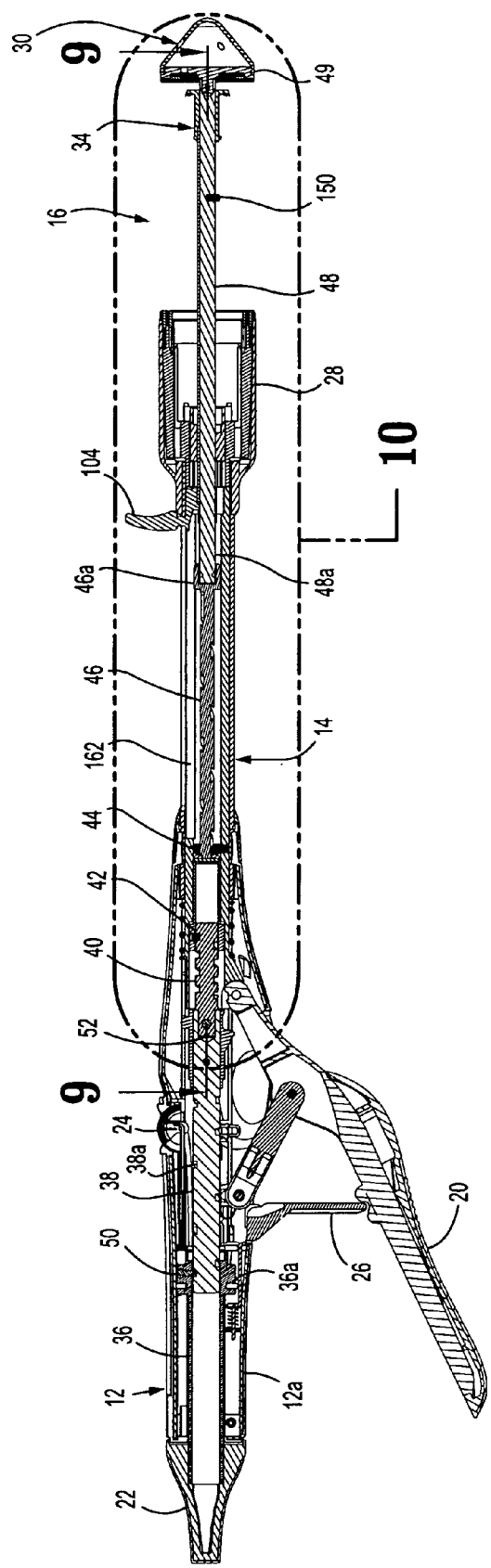
FIG. 8 is a side cross-sectional view of the surgical stapling device shown in FIG. 1, illustrating the anvil assembly in its unapproximated position.

Referring also to FIGS. 2, 6 and 7, tensioner actuator member 104 is connected to tissue tensioner 100 by link 102. Link 102 includes a proximal enlargement 102a and a distal enlargement 102b. A cutout or recess 140a (FIG. 7) dimensioned to receive enlargement 102a is formed in base 104a of actuator member 104. A cutout or recess 140b dimensioned to receive enlargement 102b is formed within throughbore 134 of tissue tensioner 100. Enlargements 102a and 102b are positioned within recesses 140a and 140b to secure actuator member 104 to tissue tensioner 100 such that movement of actuator member 104 along elongated body 14 effects movement of tissue tensioner 100 along anvil shaft 48. A stop member 150 is positioned on anvil shaft 48 at a position to limit the extent of proximal movement of tensioner 100 about anvil shaft 48. Stop member 150 may be fastened to anvil shaft 48 using, for example, screw threads. Alternately, stop member 150 may be monolithically or integrally formed with anvil shaft 48.

Turning to FIG. 14, tensioner actuator member 104 includes finger engagement member 160 which extends radially outwardly from its base 104a and is positioned to be operated by a finger or hand of an operator. Base 104a is slidably positioned within a channel 162 formed in elongated body portion 14 of stapling device 10. An intermediate member 164 of actuator member 104 extends through slot 32 formed in elongated body portion 14 to interconnect base 104a and finger engagement member 160. When engagement member 160 is slid along elongated body portion 14 of stapling device 10, tissue tensioner 100 is moved along anvil shaft 48.

FIGS. 9-14a illustrate operation of the approximation mechanism and tissue tensioner assembly 34 of surgical stapling device 10.

FIGS. 9-10a illustrate surgical stapling device 10 in the unapproximated pre-fired condition. In this condition, anvil assembly 30 is in its distal-most position with anvil head assembly 49 located at a position spaced from shell assembly 28. Tissue tensioner 100 of tissue tensioner assembly 34 is located at its distal-most position about anvil shaft 48 and actuator member 104 is positioned adjacent a proximal end of shell assembly 28 (FIG. 9a). Drive screw 38 and screw extension 40 are positioned in an advanced position within handle assembly 12 and cam member 60 is positioned in the distal end of helical channel 58 of screw extension 40 such that a void 42d is defined within extension sleeve 42. Cam member 76 is positioned within a proximal end of helical groove 70 such that pin support member 44 is positioned about the proximal end of extender shaft 46.

Surgical stapling device 10 may be used to join the ends of two lumens or to treat and/or remove a portion of a single lumen such as during a surgical procedure for the treatment of hemorrhoids, e.g., mucosectomy, hemorrhoidectomy, etc., as will be discussed in further detail below. In such procedures, distal head portion 16 is inserted into the lumen of a vessel 190, e.g., the anus, with device 10 in its unapproximated, prefired condition. A pursestring suture 192 is stitched or formed in a portion of the vessel 190 to be treated and/or removed (FIG. 9a). Next, pursestring suture 192 is tightened to collapse the inner walls of vessel 190 about tissue tensioner 100 (FIG. 10a). In one embodiment, a proximal end of hollow body 130 of tissue tensioner 100 includes annular projections 130a which prevent the pursestring suture from sliding over the proximal end of body 130.

Figure 10C:
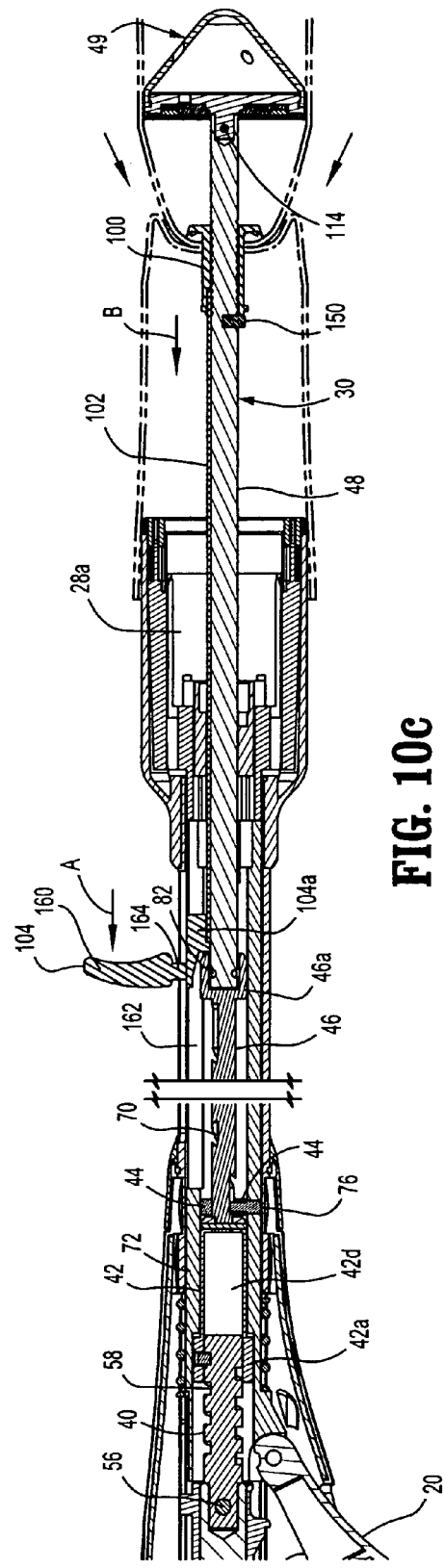
FIG. 10c is a side cross-sectional view of the distal end of the surgical stapling device shown in FIG. 10a positioned adjacent a lumen of a vessel, the anvil assembly in its unapproximated position and the tissue tensioner device in a partially retracted position.
Figures 12A, 12B:
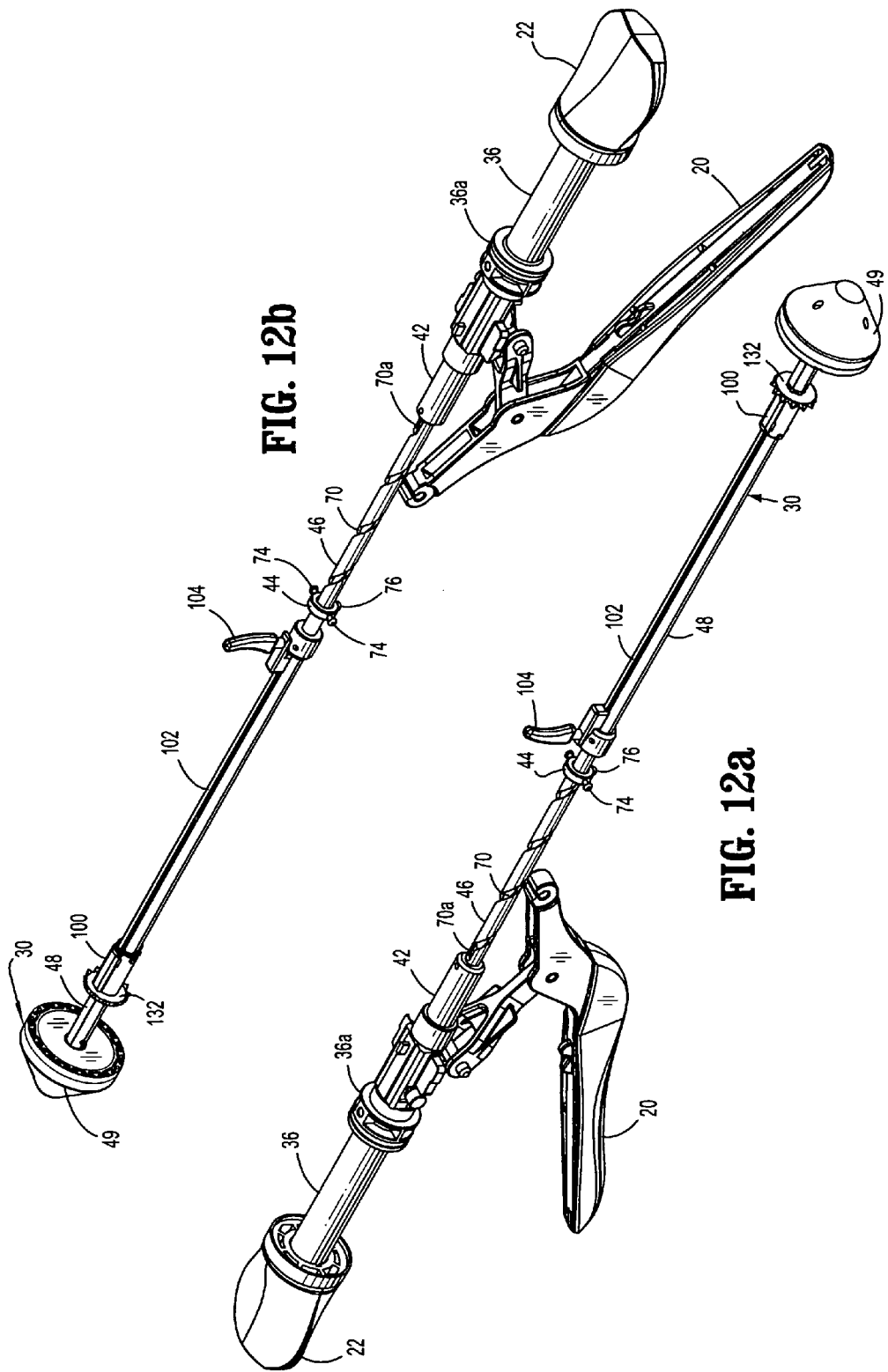
FIGS. 12a-12b are perspective views of the approximation mechanism of the surgical stapling device shown in FIG. 1, illustrating the anvil assembly in its approximated position and the tissue tensioner assembly in a fully retracted position.

Referring to 10b-12b, after lumen 210 has been collapsed about tissue tensioner 100, tissue tensioner assembly 34 can be actuated to pull the tissue of vessel 190 to be removed towards shell assembly 28 of stapling device 10. This enables the tissue to be removed to be more easily retracted into a second void 28a defined within shell assembly 28 to allow for subsequent removal of the desired tissue. It is contemplated that tissue tensioner assembly 34 may be actuated to reposition tissue tensioner 100 on anvil shaft 48 a multiplicity of times and/or at any degree of approximation of device 10. Tissue tensioner assembly 34 is actuated by pulling actuator member 104 proximally as indicated by arrow "A" in FIG. 10c. Proximal movement of actuator member 104 is translated by link 102 to tissue tensioner 100 such that tissue tensioner 100 is moved proximally as indicated by arrow "B" in FIG. 10c along anvil shaft 48. As shown in FIGS. 10 and 10d, discussed above, as tissue tensioner 100 moves proximally over anvil shaft 48, spring detent 136 which is positioned on spring arm 136a sequentially engages axially spaced teeth 138 formed on anvil shaft 48 to selectively retain tissue tensioner 100 at any one of a multiplicity of positions along anvil shaft 48. Engagement between teeth 138 and detent 136 causes spring arm 136a to deflect upwardly to move detent 136 over teeth 138 during longitudinal movement of tissue tensioner 100. Stop member 150 defines the proximal-most position of tissue tensioner 100 on anvil shaft 48. In its proximal-most position, tissue tensioner 100 should be positioned in the proximal portion of void 28a of shell assembly 28 when stapling device 10 is fully approximated. As such, tissue tensioner 100 typically will be retractable about ½ inch (12.7 mm) to about 1 inch (25.4 mm), and in one embodiment about ¾ inch (19.05 mm). However, the distance tissue tensioner will retract will vary in proportion to the overall length of the shell assembly and the length of the shell assembly may be selected based upon its selected use. As such, it is envisioned that the length of retraction of tissue tensioner 100 may exceed 1 inch or be less than ½ inch.

Figure 13A:
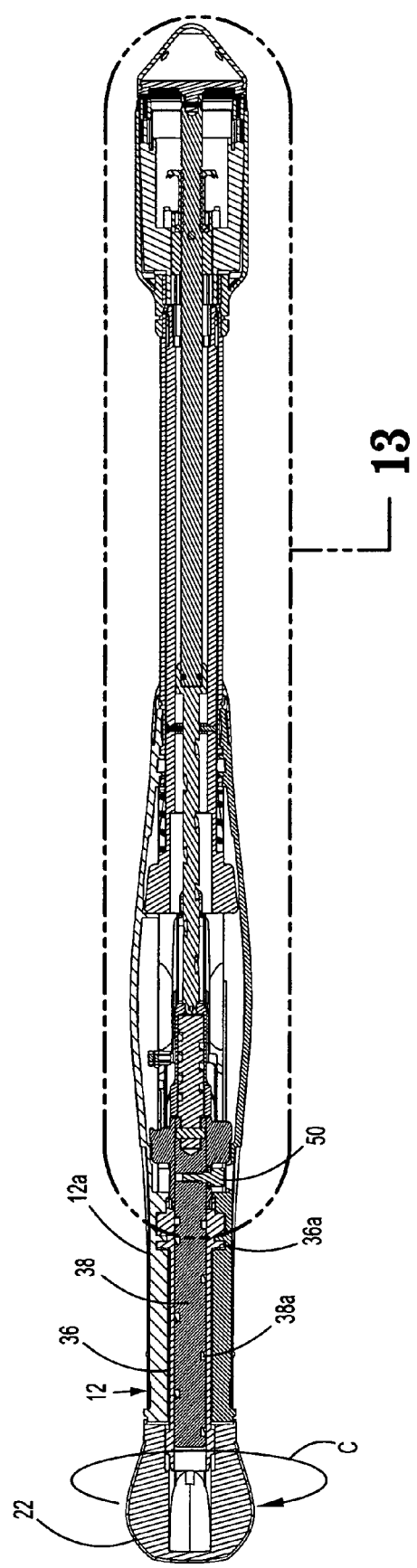
FIG. 13a is a top cross-sectional view of the surgical stapling device shown in FIG. 1 illustrating rotation of the rotatable approximation knob to approximate the anvil assembly.

Referring to FIGS. 13a-14, when approximation knob 22 is rotated in the direction indicated by arrow "C" in FIG. 13a, sleeve 36 rotates about drive screw 38 to drive pin 50 along helical groove 38a of drive screw 38 and to draw drive screw 38 proximally into sleeve 36. Since screw extension 40 is secured to drive screw 38 by coupling member 56, proximal movement of drive screw 38 effects proximal movement of screw extension 40.

Cam member 60 (FIG. 14) extends inwardly from extension sleeve 42 into helical channel 58 of screw extension 40. As screw extension 40 moves linearly in relation to extension sleeve 42, cam member 60 is forced to move through helical channel 58 to effect rotation of extension sleeve 42 about its longitudinal axis. Since extension sleeve 42 is secured to extender shaft 46 by pin 64, as extension sleeve 42 is rotated about its longitudinal axis, extender shaft 46 is also rotated about its longitudinal axis.

As best seen in FIG. 13, pin support member 44 is fixedly secured to pusher 72 of stapling device 10. Pusher 72 is stationary within elongated body 14 during approximation of stapling device 10. Thus, cam member 76, which extends through pin support member 44 into helical groove 70 of extender shaft 46, remains stationary within elongated body portion 14 during approximation of stapling device 10. As extender shaft 46 rotates within elongated body 14, cam member 76 moves along helical groove 70 to move extender shaft 46 and extension sleeve 42 proximally in relation to drive screw 38 and screw extension 40. Since extender shaft 46 is rotatably coupled to anvil shaft 48, anvil shaft 48 is moved proximally with extender shaft 46. Relative movement between drive screw 38 and extender shaft 46 allows for the input stroke of drive screw 38 to be amplified into a greater output stroke of the anvil shaft 48. As such, the length of movement of the anvil head assembly 49 in relation to shell assembly 28 can be greatly extended without having to change the length of drive screw 32 and/or handle assembly 12. The ability to provide greater spacing between anvil head assembly 49 and shell assembly 28 in a compact instrument allows for improved visibility at the surgical site and simplifies access to the surgical site.

As illustrated in FIG. 14, when stapling device 10 has been fully approximated, screw extension 40 is positioned within void 42d of extension sleeve 42. It is noted that anvil shaft 48 has a hexagonal cross-section and is slidably received through a correspondingly shaped bore (not shown) in shell assembly 28. Thus, anvil shaft 48 only moves linearly and does not rotate with extender shaft 46.

Figure 15:
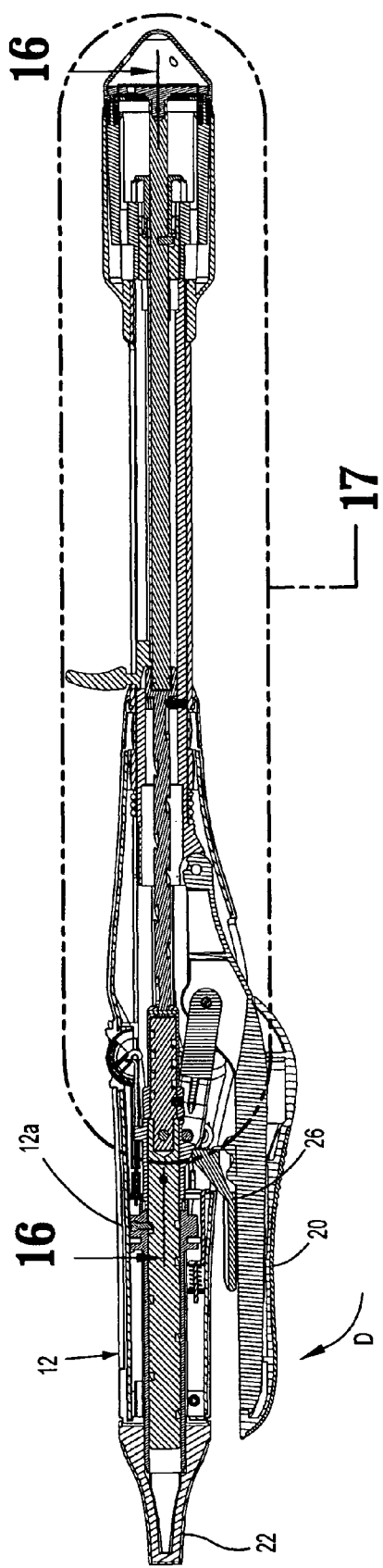
FIG. 15 is a side cross-sectional view of the surgical stapling device shown in FIG. 1 illustrating actuation of the firing trigger of the handle mechanism.
Figure 23:
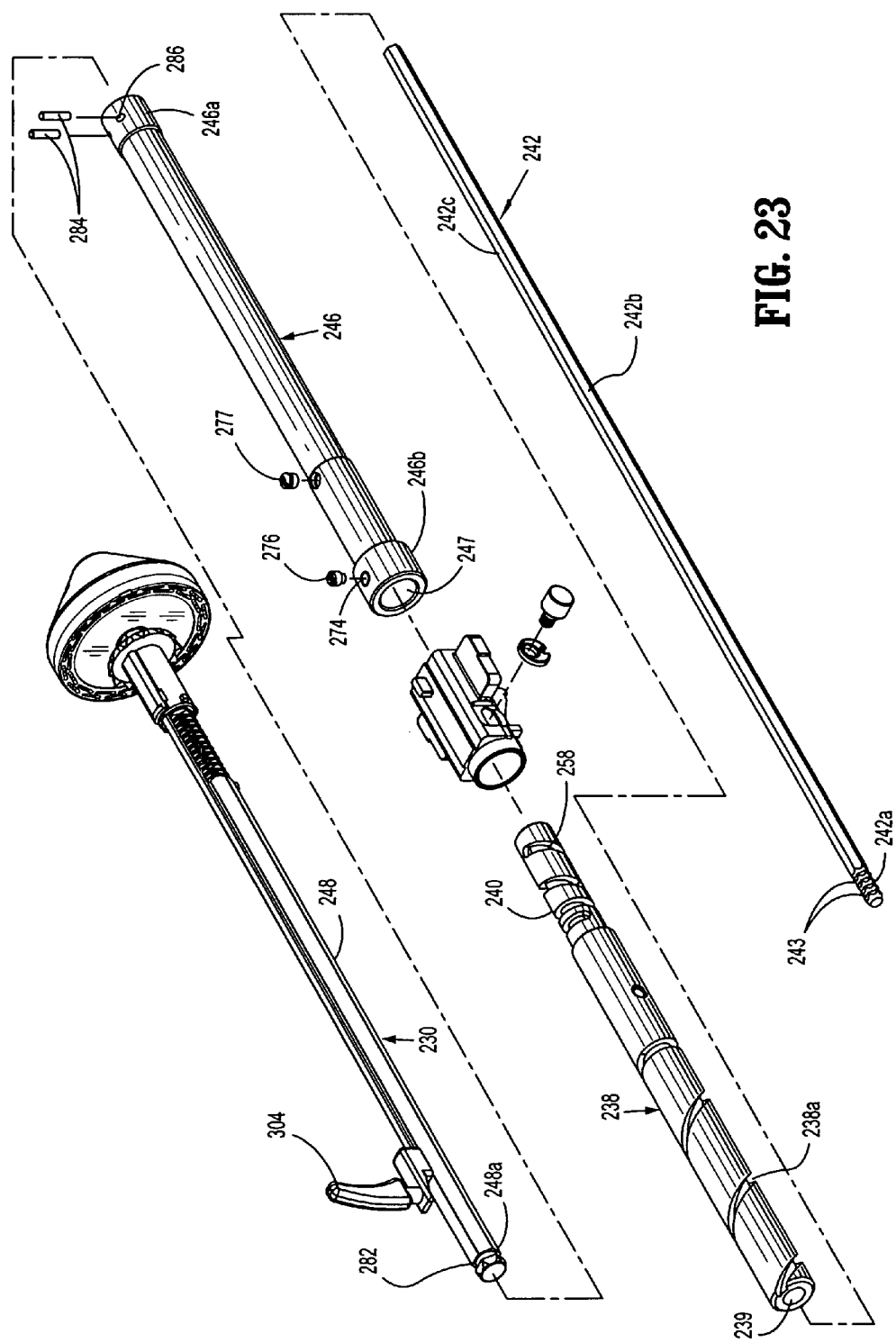
FIG. 23 is a perspective view with parts separated of the approximation mechanism of the surgical stapling device shown in FIG. 18.
Figure 24:
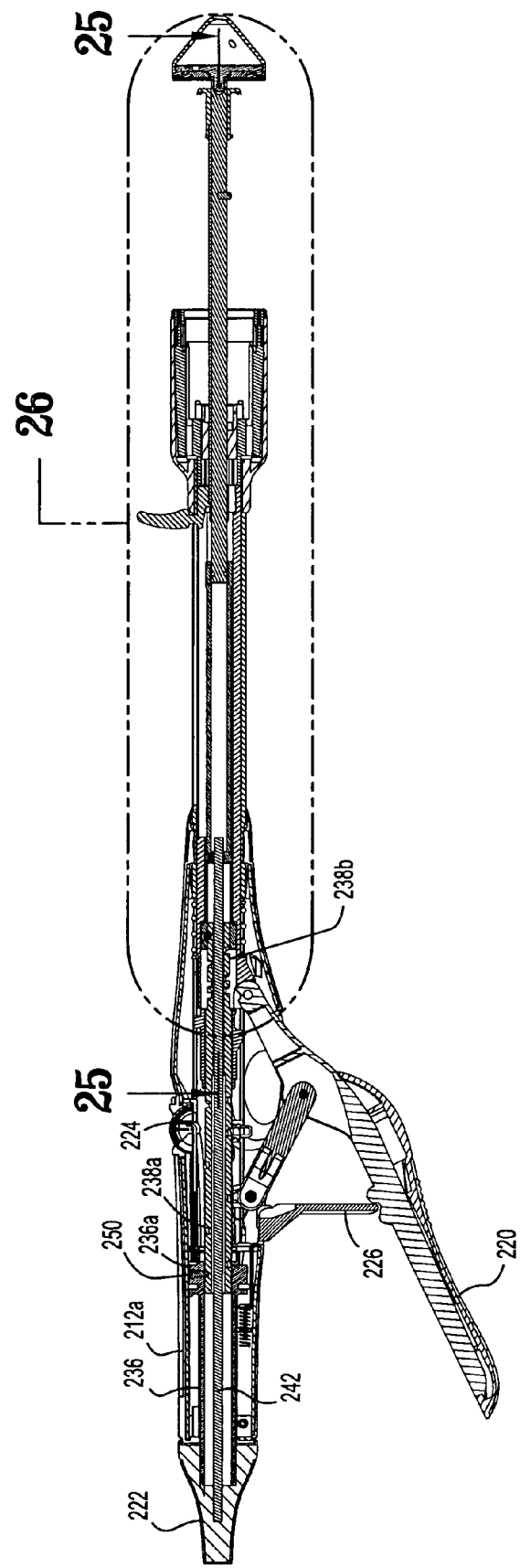
FIG. 24 is a side cross-sectional view of the surgical stapling device shown in FIG. 18.
Figure 36:
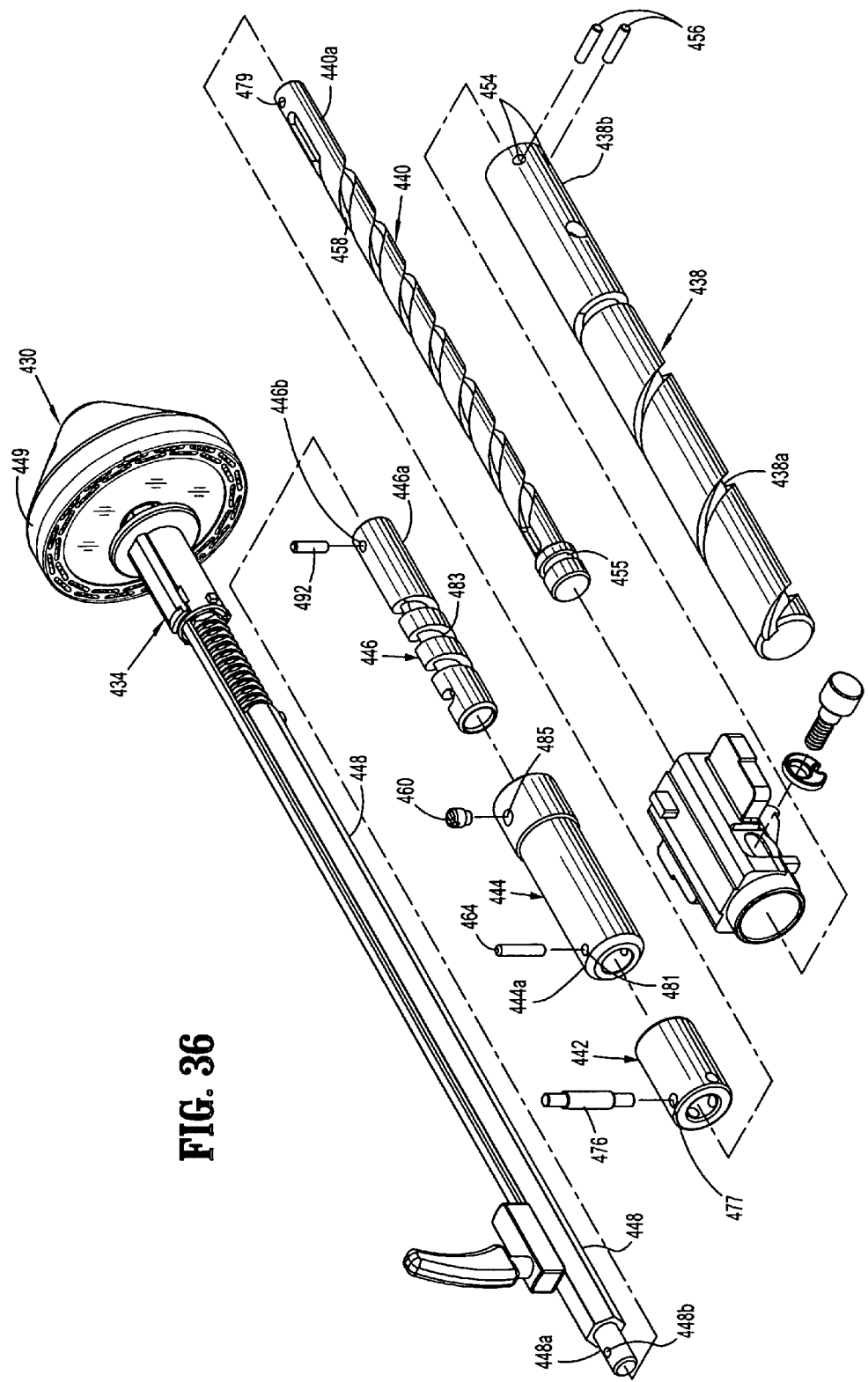
FIG. 36 is a perspective view with parts separated of the approximation mechanism of the surgical stapling device shown in FIG. 34.

Referring to FIGS. 15-17, after stapling device 10 has been approximated, firing trigger lockout 26 can be pivoted towards housing 12a of handle assembly 12 and firing trigger 20 can be pivoted in the direction indicated by arrow "D" in FIG. 15 to eject staples from shell assembly 28 and core tissue. Operation of the firing mechanism is described in detail in the '074 and '841 applications and will not be discussed in detail herein. As shown in FIG. 17, when firing trigger 20 is pivoted, pusher 72 is moved distally within elongated body 14. Since pin support member 44 is secured to pusher 72, pin support member 44 is also moved distally with pusher 72. In the approximated condition of stapling device 10, pin 76 of pin support member 44 is positioned in linear section 70a of helical groove 70. As such, during actuation of the firing mechanism of stapling device 10, distal movement of pin support member 44 advances pin 76 through linear section 70a of helical groove 70 and does not cause further movement of extender shaft 46.

FIGS. 18-33 illustrate another embodiment of the presently disclosed surgical stapling device shown generally as 200. Referring to FIGS. 18 and 19, surgical stapling device 200 includes a handle assembly 212, an elongated body portion 214, a distal head portion 216 and a tissue tensioner assembly 234. Although elongated body portion 214 is shown as being substantially straight, it is contemplated, as is known in the art, to provide a curved body portion.

As disclosed with reference to surgical stapling device 10, handle assembly 212 includes a housing 212a defining a grip 218, a firing trigger 220, a rotatable approximation knob 222, a firing indicator 224 and a firing trigger lockout 226. Each of these components functions substantially as described in the '074 and '841 applications and will not be discussed in detail herein.

Head portion 216 includes a shell assembly 228 and an anvil assembly 230. Shell assembly 228 is secured to a distal end of elongated body portion 214. Elongated body portion 214 includes an elongated slot 232 for slidably receiving a tensioner actuation member 304 of tissue tensioner assembly 234 which will be described in further detail below.

Handle assembly 212 includes the proximal components of the approximation and firing mechanisms of surgical stapling device 200, a firing lockout mechanism and an indicator mechanism. The firing mechanism, the firing lockout mechanism and the indicator mechanism are substantially as described in the '074 and '841 applications will not be described in detail herein. The approximation mechanism of device 200 has been modified from that described in the '074 and '841 applications to provide better visibility of and improved access to the surgical site. These modifications will now be discussed.

Referring to FIGS. 21-28, the approximation mechanism includes rotatable approximation knob 222, a rotatable sleeve 236, a drive screw 238, a screw extension 240, a drive shaft 242 (FIG. 23), and an extender 246. The distal end of the tubular extender 246 is rotatably coupled to a proximal end 248a of an anvil shaft 248 of anvil assembly 230. When approximation knob 222 is rotated or actuated, anvil assembly 230 is moved in relation to shell assembly 228 (FIG. 24) between spaced and approximated positions in a manner described below.

Approximation knob 222 is secured to the proximal end of rotatable sleeve 236 using any known fastening technique, e.g., pins, adhesives, key/slot arrangement, welding, etc. The distal end of rotatable sleeve 236 is rotatably secured with handle assembly housing 212a (FIG. 24) in the manner described in the '074 application. A pin 250 (FIG. 24) extends through distal end 236a of rotatable sleeve 236 and is received within a helical groove 238a of drive screw 238. When sleeve 236 is rotated by rotating approximation knob 222, pin 250 moves within helical groove 238a of drive screw 238 to move drive screw 238 axially within housing 212a of handle assembly 212.

A distal end 238b (FIG. 23) of drive screw 238 includes screw extension 240. Screw extension 240 includes a helical channel 258 formed about an outer surface thereof. In one embodiment, helical channel 258 has a pitch of between about 0.06 thousandths/revolution and about 0.40 thousandths/revolution, and in a particularly useful embodiment, channel 258 has a pitch of about 0.120 thousandths/revolution to about 0.330 thousandths/revolution. When drive screw 238 is moved axially by rotating approximation knob 222, screw extension 240 is also moved axially within housing 212a of handle assembly 212. It is envisioned that drive screw 238 and screw extension 240 may be formed as separate components which are fixedly attached using, for example, a pin or pins.

Drive screw 238 and screw extension 240 are tubular and define an axial passage 239 therethrough. Drive shaft 242 has a proximal end 242a which is fixedly attached to approximation knob 222 such that rotation of approximation knob 222 effects rotation of drive shaft 242. In one embodiment, proximal end 242a includes a series of ridges 243 and approximation knob 222 is molded about proximal end 242a. Other techniques for fastening drive shaft 242 to approximation knob 222 are contemplated. Drive shaft 242 has an elongated body 242b having at least one longitudinally extending flat surface 242c. In one embodiment, body 242a has a hexagonal transverse cross-section (FIG. 27). Drive shaft 242 extends through throughbore 239 of drive screw 238 and screw extension 240 into a longitudinal throughbore 247 defined by extender 246.

A proximal end 246b of extender 246 includes a transverse opening 274 dimensioned to receive a cam member 276. Screw extension 240 is positioned within proximal end 246b of tubular extender 246 such that cam member 276 is slidably positioned within helical channel 258 of screw extension 240. A set screw 277 (FIG. 27) extends through a central portion of tubular extender 246 and is positioned adjacent to or abuts one of the at least one longitudinally extending flat surfaces 242c of drive shaft 242. Set screw 277 functions to rotatably secure drive shaft 242 to extender 246, while permitting axial movement of drive shaft 242 in relation to extender 246.

Referring to FIGS. 29-33, in use, when approximation knob 222 is actuated or rotated as illustrated by arrow "G" in FIG. 29, drive screw 238 is retracted or moved axially into handle assembly 212 and drive shaft 242 is rotated about its longitudinal axis. Since extender 246 is rotatably fixed to drive shaft 242 by set screw 277, extender 246 is also rotated about its longitudinal axis. As extender 246 rotates, cam member 276 is driven along helical channel 258 of screw extension 240 to effect axial movement of extender 246 in relation to drive screw 238.

A distal end of extender 246 includes a hub portion 246a dimensioned to receive a proximal end 248a of anvil shaft 248 of anvil assembly 230. The proximal end 248a of anvil shaft 248 includes an annular channel 282. A pair of pins 284 extend through openings 286 formed in hub portion 246a of tubular extender 246 through a portion of annular channel 282 to axially fix and rotatably secure tubular extender 246 to anvil shaft 248. Thus, when extender 246 is moved axially in response to rotation of approximation knob 222, anvil shaft 248 is moved axially to move an anvil head assembly 249 in relation to shell assembly 228. The distance of travel of anvil head assembly 249 in relation to shell assembly 228 will be equal to the distance drive screw 238 moves axially plus the distance extender 246 moves axially in relation to screw extension 240. Thus, the distance of travel of anvil head assembly 249 is greater than the distance of travel of drive screw 238.

Anvil assembly 230 and tissue tensioner assembly 234 are substantially similar to anvil assembly 30 and tissue tensioner assembly 34 as described above and will not be discussed in further detail herein.

Figure 37:
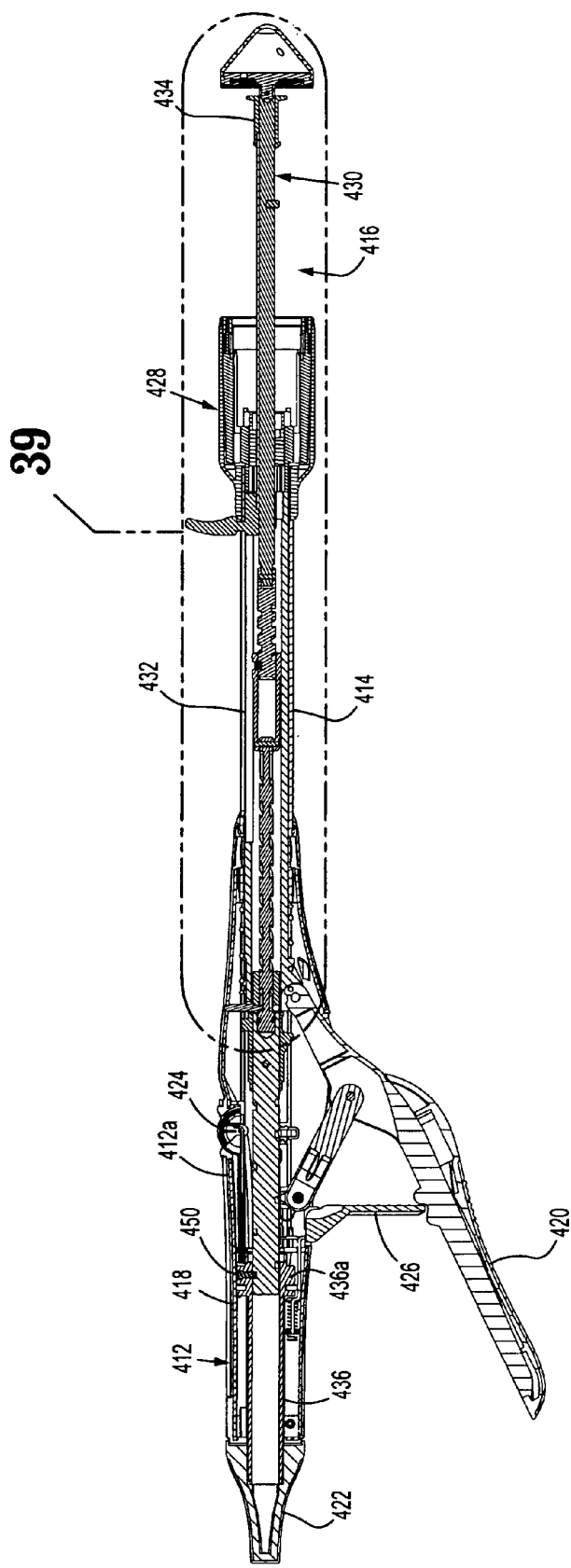
FIG. 37 is a side cross-sectional view of the surgical stapling device of the present disclosure illustrating the anvil assembly in its unapproximated position.
Figure 40:
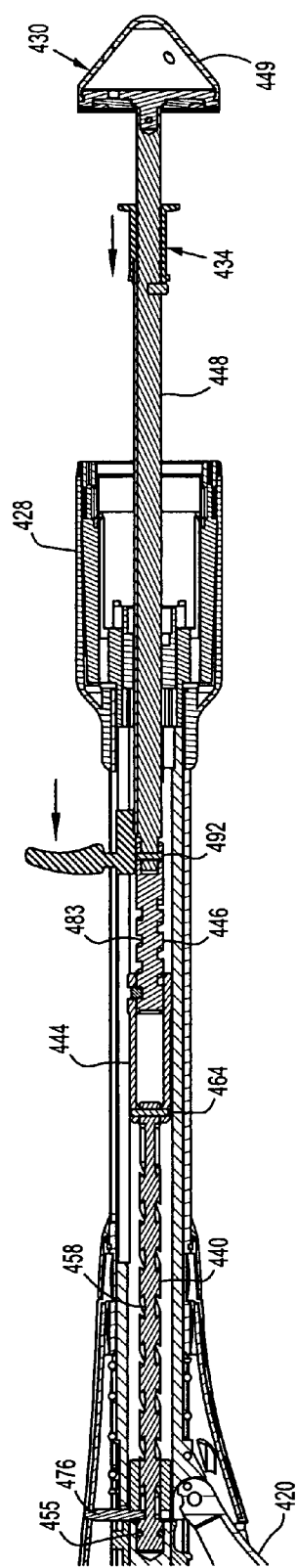
FIG. 40 is a side cross-sectional view of the distal end of the surgical stapling device illustrating actuation of the tissue tensioner device.
Figure 41:
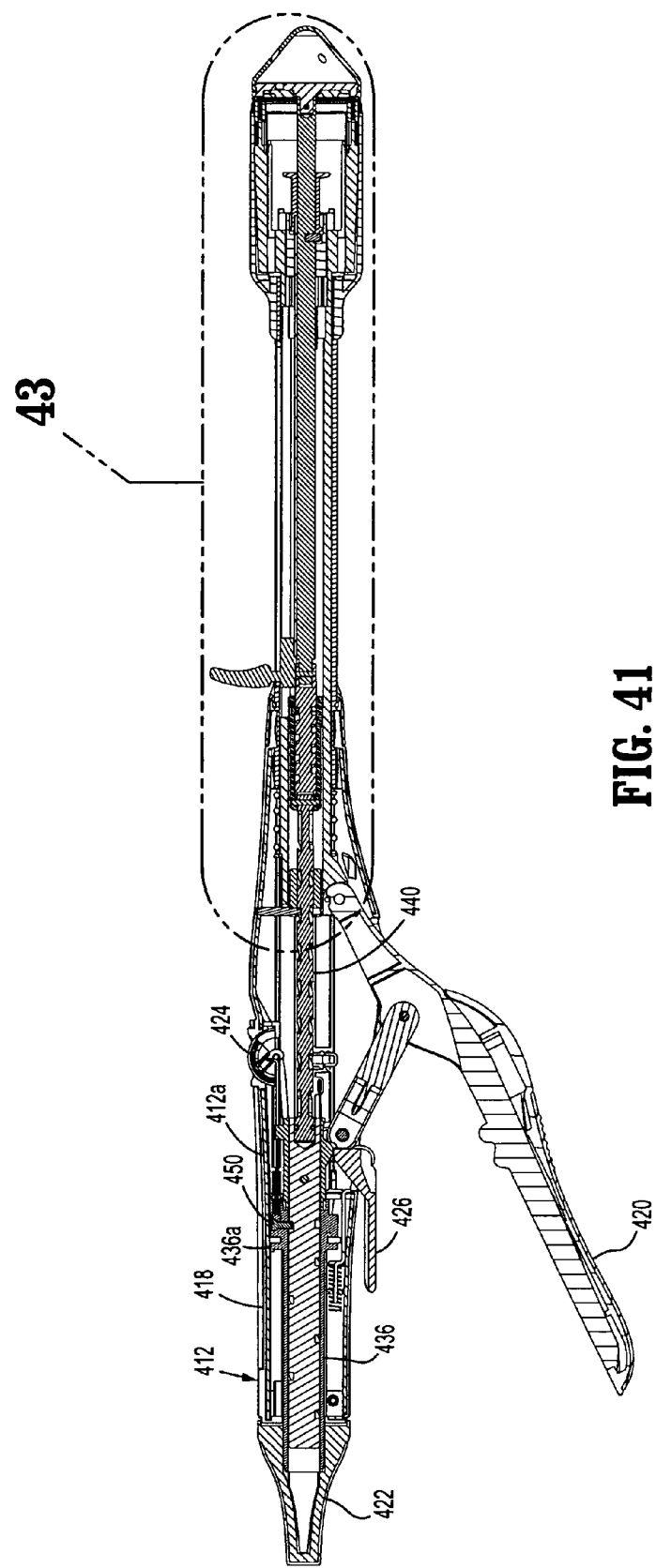
FIG. 41 is a side cross-sectional view of the surgical stapling device shown in FIG. 34 illustrating the anvil assembly in its approximated position and the tissue tensioner in a fully retracted position.

FIGS. 34-45 illustrate another embodiment of the presently disclosed surgical stapling device shown generally as 400. Referring to FIG. 37, surgical stapling device 400 includes a handle assembly 412, an elongated body portion 414, a distal head portion 416 and a tissue tensioner assembly 434. Although elongated body portion 414 is shown as being substantially straight, it is contemplated, as is known in the art, to provide a curved body portion.

As disclosed with reference to surgical stapling device 10, handle assembly 412 includes a housing 412a defining a grip 418, a firing trigger 420, rotatable approximation knob 422, a bulbous firing indicator 424 and a firing trigger lockout 426. Each of these components functions substantially as described in the '074 and '841 applications and will not be discussed in detail herein.

Head portion 416 includes a shell assembly 428 and an anvil assembly 430. Shell assembly 428 is secured to a distal end of elongated body portion 414. Elongated body portion 414 includes an elongated slot 432 for slidably receiving a tensioner actuation member 504 of tissue tensioner assembly 434 which will be described in further detail below.

Handle assembly 412 includes the proximal components of the approximation and firing mechanisms of surgical stapling device 400, a firing lockout mechanism and an indicator mechanism. The firing mechanism, the firing lockout mechanism and the indicator mechanism are substantially as described in the '074 and '841 applications and will not be described in detail herein. The approximation mechanism of device 400 has been modified from that described in the '074 and '841 applications to provide better visibility of and improved access to the surgical site. These modifications will now be discussed.

Referring to FIGS. 34-39, the approximation mechanism includes rotatable approximation knob 422, a rotatable sleeve 436, a drive screw 438, a screw extension 440, a pin support member 442, an extension sleeve 444, and an extender 446. A distal end 446a of extender 446 is secured to a proximal end 448a of an anvil shaft 448 of anvil assembly 430. When approximation knob 422 is rotated or actuated, anvil assembly 430 is moved axially in relation to shell assembly 428 between spaced and approximated positions in a manner described below.

Approximation knob 422 is secured to the proximal end of rotatable sleeve 436 using any known fastening technique, e.g., pin(s), adhesives, key/slot arrangement, welding, etc. The distal end 436a of rotatable sleeve 436 is rotatably secured within handle assembly housing 412a (FIG. 37) in the manner described in the '074 application. A pin 450 (FIG. 37) extends through distal end 436a of rotatable sleeve 436 and is received within a helical groove 438a of drive screw 438. When sleeve 436 is rotated by rotating approximation knob 422, pin 450 moves within helical groove 438a to move drive screw 438 axially within housing 412a of handle assembly 412.

A distal end 438b of drive screw 438 includes an axial bore 452 (FIG. 38) and a pair of transverse throughbores 454. The proximal end of screw extension 440 is dimensioned to be received within axial bore 452 and includes an annular channel 455. A pair of pins 456 are positioned through throughbores 454 into annular channel 455 to rotatably secure screw extension 440 to drive screw 438. When drive screw 438 is moved axially by rotating approximation knob 422, this movement is translated to axial movement of screw extension 440.

The outer surface of screw extension 440 includes a helical channel 458. In one embodiment, helical channel 458 has a pitch of between about 0.06 thousandths/revolution and about 0.40 thousandths/revolution and, in a particularly useful embodiment, channel 458 has a pitch of about 0.120 thousandths/revolution to about 0.330 thousandths/revolution. A pin support member 442 is fixedly secured to housing 412a of handle assembly 412 by a pin 476. In one embodiment, pin support member 442 is configured as an annular collar which is positioned about screw extension 440. Pin 476 extends through an opening 477 in pin support member 442 into helical channel 458 of screw extension 440. Thus, when screw extension 440 is moved axially in response to rotation of approximation knob 422, pin 476 which is axially fixed at one end to handle assembly 412 moves through helical channel 458 of screw extension 440 to effect rotation of screw extension 440 in relation to drive screw 438.

A distal end 440a of screw extension 440 is dimensioned to be received within extension sleeve 444 and includes a throughbore 479. A proximal end 444a of extension sleeve 444 also includes a throughbore 481. A pin 464 extends through throughbores 479 and 481 of screw extension 440 and extension sleeve 444, respectively, to fixedly secure screw extension 440 to extension sleeve 444. Accordingly, when screw extension 440 is driven to rotate by pin 476, extension sleeve 444 will also rotate about its longitudinal axis.

Extender 446 is positioned within extension sleeve 444. A helical channel 483 is formed about extender 446. Helical channel 483 is dimensioned to receive a cam member 460 which extends through an opening 485 formed in extension sleeve 444. When extension sleeve 444 is rotated about its longitudinal axis, cam member 460 moves through helical channel 483 to effect axial movement of extender 446 in relation to extension sleeve 444.

The distal end 446a of extender 446 includes an axial bore 490 dimensioned to receive the proximal end 448a of anvil shaft 448. An opening 446b is formed in the distal end of extender 446 and an opening 448b is formed in the proximal end 448a of anvil shaft 448. A pin 492 extends through openings 446b and 448b to fixedly secure anvil shaft 448 to extender 446.

Referring to FIGS. 40-45, in use, when approximation knob 422 is rotated to move drive screw 438 axially within housing 412a of handle assembly 412, screw extension 440 is moved axially with drive screw 438. As screw extension 440 moves axially, pin 476 which is supported on pin support member 442 moves within helical channel 458 of screw extension 440 to effect rotation of screw extension 440 in relation to drive screw 438. Since extension sleeve 444 is secured to screw extension 440 by pin 464, extension sleeve 444 rotates with screw extension 440. As extension sleeve 424 rotates, cam member 460 moves within helical channel 483 of extender 446 to effect axial movement of extender 446 in relation to extension sleeve 424. Since anvil shaft 448 is secured to distal end 440a of screw extension 440, axial movement of extender 446 effects axial movement of anvil shaft 448. The overall axial distance anvil head assembly 449 will move in relation to shell assembly 30 will be the axial distance drive screw 438 moves plus the axial distance extender 446 moves in relation to extender sleeve 444.

As shown in FIGS. 34-39, tissue tensioner assembly 434 is formed as a substantially flat circular disk. It is contemplated that the tissue tensioner assembly 434 is operable without the provision of serrations as shown in previous embodiments. The operation and function of anvil assembly 430 and tissue tensioner assembly 434 are substantially similar to anvil assembly 30 and tissue tensioner assembly 34 and will not be discussed in further detail herein.

The presently disclosed surgical stapling devices are particularly suitable for use in surgical procedures for hemorrhoid treatment. Such procedures include hemorrhoidectomies and procedures to reduce mucosa membrane prolapse. During a hemorrhoidectomy procedure, some or all of a hemorrhoid(s) is removed by the surgical stapler. One such hemorrhoidectomy procedure is described in an article entitled "Removal of internal hemorrhoidal modules by means of devices designed for the application of circular anastomoses" by Mikall Yur'evich Kozubenko, located in the Ministry of Health of the USSR, Ukranian Institute for Advanced Medical Training on Aug. 13, 1991. This article is incorporated herein by reference in its entirety. During a procedure for reducing mucosa membrane prolapse, a transverse section of mucous is excised between the ampulla recti and the anal canal to restore the normal anatomical relationship between the anal mucosa and the hemorrhoidal piles with the anal sphincters. Such a procedure for reducing mucosa membrane prolapse is described in the article "Treatment of Hemorrhoids disease by reduction of mucosa and hemorrhoidal prolapse with a circular suturing device: a new procedure" by A. Longo, published in Congress of Endoscopic Surgery, Jun. 3-6, 1998, which is also incorporated herein in its entirety by reference.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended hereto. Having thus described the invention with the details and particularity required by the patent laws, what is claimed and desired protected is set forth in the appended claims.

What is claimed is:

1. A surgical stapling device comprising:
   an elongated body portion;
   a distal head portion including an anvil assembly and a shell assembly supported on the distal end of the elongated body portion, the anvil assembly including an anvil head assembly and an anvil shaft, the shell assembly supporting a plurality of staples, the anvil assembly being movable in relation to the shell assembly between spaced and approximated positions; and
   an approximation mechanism including a rotatable approximation knob, a drive member, and an extension mechanism, the approximation knob being operably connected to the drive member and being actuable to effect axial movement of the drive member over a first distance;
   wherein the extension mechanism operably connects the drive member to the anvil shaft such that axial movement of the drive member over the first distance effects axial movement of the anvil shaft over a second distance which is greater than the first distance.

2. A surgical stapling device according to claim 1, wherein the extension mechanism includes an elongated drive shaft having a proximal end fixedly connected to the approximation knob and a distal end rotatably fixed to a tubular extender such that rotation of the approximation knob effects rotation of the drive shaft and rotation of the tubular extender.

3. A surgical stapling device according to claim 2, wherein the distal end of the tubular extender is operably connected to the anvil shaft.

4. A surgical stapling device according to claim 3, wherein the drive member includes a longitudinal bore and the drive shaft extends through the longitudinal bore.

5. A surgical stapling device according to claim 4, wherein the drive member includes a distal extension having a helical groove formed thereabout and the tubular extender includes a cam member positioned to be received within the helical groove, wherein actuation of the approximation knob effects rotation of the drive shaft and rotation of the tubular extender, and rotation of the tubular extender about the distal extension of the drive member effects movement of the cam member within the helical groove to effect axial movement of the tubular extender in relation to the drive member over the second distance.

6. A surgical stapling device according to claim 5, wherein the distal end of the tubular extender is rotatably connected to the proximal end of the anvil shaft.

7. A surgical stapling device according to claim 6, wherein the elongated drive shaft includes at least one flat surface and the tubular extender includes a set screw positioned to engage the at least one flat surface to rotatably fix the tubular extender to the drive shaft.

8. A surgical stapling device according to claim 1, wherein the extension mechanism includes an extension sleeve having a cam member supported thereon and an extender fixedly attached to the proximal end of the anvil shaft, the extension sleeve translating axial movement of the drive screw to axial movement of the extension sleeve.

9. A surgical stapling device according to claim 8, further including a drive member extension rotatably coupled to the distal end of the drive member, the distal end of the drive member extension being fixedly secured to the extension sleeve.

10. A surgical stapling device according to claim 9, wherein the drive member extension includes a first helical groove formed thereabout, the first helical groove being dimensioned to receive a pin which is fixedly secured to the stapling device, such that axial movement of the drive member extension in relation to the pin effects rotation of the drive member extension and the extension sleeve in relation to the drive member.

11. A surgical stapling device according to claim 10, wherein the extender includes a second helical groove formed thereabout, the second helical groove being dimensioned to receive the cam member supported on the extension sleeve such that rotation of the extension sleeve in relation to the extender effects axial movement of the extender and the anvil shaft in relation to the drive member over the second distance.

12. A surgical stapling device according to claim 1, further comprising a tissue tensioner assembly including a tissue engaging member, the tissue engaging member being positioned between the anvil assembly and the shell assembly and movable in relation to the anvil assembly and in relation to the shell assembly.

13. A surgical stapling device according to claim 9, wherein the tissue tensioner assembly includes a hollowed body having a locking member positioned to releasably engage a ratchet portion of the anvil shaft.

* * * * *